(12) United States Patent
Hansen et al.

(10) Patent No.: US 11,701,248 B2
(45) Date of Patent: Jul. 18, 2023

(54) ACCESSORY DEVICES OF A MEDICAL SYSTEM, AND RELATED METHODS FOR COMMUNICATING LEAKAGE STATE

(71) Applicant: Coloplast A/S, Humlebaek (DK)

(72) Inventors: Jais Ask Hansen, Jaegerspris (DK); Niels Hvid, Vedbaek (DK); Daniel Gewecke Daugaard-Jensen, Frederiksberg (DK); Peter Flintholm Soerensen, Aarhus C (DK); Dan Boegsted Andersen, Copenhagen OE (DK); Finn Speiermann, Virum (DK)

(73) Assignee: Coloplast A/S, Humlebaek (DK)

( * ) Notice: Subject to any disclaimer, the term of this patent is extended or adjusted under 35 U.S.C. 154(b) by 312 days.

(21) Appl. No.: 16/955,038

(22) PCT Filed: Dec. 20, 2018

(86) PCT No.: PCT/DK2018/050396
§ 371 (c)(1),
(2) Date: Jun. 18, 2020

(87) PCT Pub. No.: WO2019/120440
PCT Pub. Date: Jun. 27, 2019

(65) Prior Publication Data
US 2020/0375783 A1 Dec. 3, 2020

(30) Foreign Application Priority Data
Dec. 22, 2017 (DK) .......................... PA 2017 70997

(51) Int. Cl.
*A61F 5/44* (2006.01)
*A61B 5/00* (2006.01)
(Continued)

(52) U.S. Cl.
CPC ............ *A61F 5/4404* (2013.01); *A61B 5/053* (2013.01); *A61B 5/6843* (2013.01); *A61B 5/742* (2013.01);
(Continued)

(58) Field of Classification Search
CPC .................... A61B 18/1206; A61B 2017/1482
(Continued)

(56) References Cited

U.S. PATENT DOCUMENTS

| 2,054,535 A | 9/1936 | Diack |
| 2,327,514 A | 8/1943 | Fenwick |

(Continued)

FOREIGN PATENT DOCUMENTS

| CN | 203786580 U | 8/2014 |
| CN | 104902399 A | 9/2015 |

(Continued)

*Primary Examiner* — Fabricio R Murillo Garcia
(74) *Attorney, Agent, or Firm* — Coloplast Corp., Coloplast A/S; Nick Baumann

(57) ABSTRACT

The present disclosure provides a method, performed in an accessory device, for communicating a leakage state of an ostomy appliance, wherein the accessory device comprises an interface configured to communicate with one or more devices of an ostomy system, the one or more devices comprising a monitor device, and/or the ostomy appliance configured to be placed on a skin surface of a user. The method comprises obtaining monitor data from the one or more devices, the monitor data being indicative of presence of fluid at a proximal side of a first adhesive layer of the ostomy appliance towards the skin surface; determining a leakage state at the proximal side of the first adhesive layer of the ostomy appliance based on the monitor data, and communicating the leakage state of the ostomy appliance via the interface.

20 Claims, 19 Drawing Sheets

(51) Int. Cl.

| | |
|---|---|
| *G08C 17/02* | (2006.01) |
| *A61F 13/00* | (2006.01) |
| *A61F 5/445* | (2006.01) |
| *A61F 5/443* | (2006.01) |
| *A61B 5/053* | (2021.01) |
| *H04M 1/72409* | (2021.01) |
| *G16H 40/60* | (2018.01) |
| *H04M 1/72412* | (2021.01) |

(52) U.S. Cl.
CPC ............ *A61B 5/7405* (2013.01); *A61B 5/746* (2013.01); *A61B 5/7475* (2013.01); *A61F 5/443* (2013.01); *A61F 5/445* (2013.01); *A61F 13/00055* (2013.01); *G08C 17/02* (2013.01); *H04M 1/724094* (2022.02); *G16H 40/60* (2018.01); *H04M 1/72412* (2021.01)

(58) Field of Classification Search
USPC ........................................................ 604/318
See application file for complete search history.

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,165,005 A | 12/2000 | Mills et al. |
| 6,171,289 B1 | 1/2001 | Millot et al. |
| 6,206,864 B1 | 3/2001 | Kavanagh et al. |
| 6,246,330 B1 | 6/2001 | Nielsen |
| 6,297,422 B1 | 10/2001 | Hansen et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | von Dyck et al. |
| 6,520,943 B1 | 2/2003 | Wagner |
| 6,659,989 B1 | 12/2003 | Otto |
| 6,764,474 B2 | 7/2004 | Nielsen et al. |
| 7,049,478 B1 | 5/2006 | Smith |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | von Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Rdvardsen et al. |
| 8,449,471 B2 | 5/2013 | Tran |
| 8,474,338 B2 | 7/2013 | Gelman et al. |
| 8,500,718 B2 | 8/2013 | Locke et al. |
| 8,632,492 B2 | 1/2014 | DeLegge |
| 8,680,991 B2 | 3/2014 | Tran |
| 8,684,982 B2 | 4/2014 | Nguyen-DeMary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,464 B2 | 9/2014 | Hanuka et al. |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,779 B2 | 4/2017 | Grum-Schwensen et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,406,525 B2 | 8/2022 | Seres et al. |
| 11,471,318 B2 | 10/2022 | Hansen et al. |
| 11,491,042 B2 | 11/2022 | Seres et al. |
| 11,534,323 B2 | 12/2022 | Hansen et al. |
| 11,540,937 B2 | 1/2023 | Hansen et al. |
| 11,547,595 B2 | 1/2023 | Hansen et al. |
| 11,547,596 B2 | 1/2023 | Hansen et al. |
| 11,559,423 B2 | 1/2023 | Speiermann et al. |
| 11,559,426 B2 | 1/2023 | Sletten et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |

(56) References Cited

U.S. PATENT DOCUMENTS

| | | |
|---|---|---|
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise, Jr. et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries, Jr. et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Eager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow, Jr. et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1* | 2/2010 | Thirstrup ............... A61F 13/02 340/657 |
| 2010/0036206 A1 | 2/2010 | Lorio |
| 2010/0072271 A1 | 3/2010 | Thorstensson |
| 2010/0076275 A1 | 3/2010 | Chu et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-DeMary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0324952 A1* | 12/2013 | Krystek ............... A61F 5/445 604/318 |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1* | 10/2014 | Aceto ............... A61M 1/90 604/319 |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mårtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0112658 A1 | 4/2017 | Hosono |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1 | 6/2018 | Sakurai et al. |
| 2019/0133810 A1 | 5/2019 | Seres et al. |
| 2019/0133811 A1* | 5/2019 | Seres ............... A61F 5/445 |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0297244 A1* | 9/2020 | Brownhill ............ A61B 5/4836 |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |

(56) References Cited

U.S. PATENT DOCUMENTS

| | | |
|---|---|---|
| 2020/0337881 A1 | 10/2020 | Hansen et al. |
| 2020/0337883 A1 | 10/2020 | Hansen et al. |
| 2020/0375499 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0007663 A1 | 1/2021 | Svanegaard et al. |
| 2021/0007881 A1 | 1/2021 | Svanegaard et al. |
| 2021/0015654 A1 | 1/2021 | Hansen et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0177642 A1 | 6/2021 | Andersen et al. |
| 2021/0212855 A1 | 7/2021 | Hansen et al. |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Feam et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0800804 B1 | 6/2003 |
| EP | 1188157 B1 | 12/2005 |
| EP | 2108345 A1 | 10/2009 |
| EP | 1275357 B1 | 3/2011 |
| EP | 2000083 B1 | 8/2012 |
| EP | 2601915 A1 | 6/2013 |
| EP | 2738960 A1 | 6/2014 |
| EP | 2489561 B1 | 8/2014 |
| EP | 2654646 B1 | 7/2016 |
| EP | 3226946 A1 | 10/2017 |
| EP | 3213727 B1 | 12/2019 |
| EP | 3064179 B1 | 9/2021 |
| GB | 2219679 A | 12/1989 |
| GB | 2308306 B | 9/1999 |
| GB | 2343628 A1 | 5/2000 |
| GB | 2465742 B | 7/2012 |
| GB | 2486968 B | 2/2015 |
| GB | 2542093 A | 3/2017 |
| GB | 2561193 B | 9/2020 |
| JP | H0474882 A | 3/1992 |
| JP | H06152077 A | 5/1994 |
| JP | H0910184 A | 1/1997 |
| JP | 2000093448 A | 4/2000 |
| JP | 2001087299 A | 4/2001 |
| JP | 2002055074 A | 2/2002 |
| JP | 2002224093 A | 8/2002 |
| JP | 2005323981 A | 11/2005 |
| JP | 2007319561 A | 12/2007 |
| JP | 2009519751 A | 5/2009 |
| JP | 2014033745 A | 2/2014 |
| JP | 2014054368 A | 3/2014 |
| KR | 101056989 B1 | 8/2011 |
| KR | 20120003987 A | 1/2012 |
| KR | 200485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 1994015562 A1 | 7/1994 |
| WO | 1997010012 A1 | 3/1997 |
| WO | 1999033037 A1 | 7/1999 |
| WO | 1999036017 A1 | 7/1999 |
| WO | 2000079497 A1 | 12/2000 |
| WO | 2001013830 A1 | 3/2001 |
| WO | 2001050996 A1 | 7/2001 |
| WO | 2002052302 A2 | 7/2002 |
| WO | 2002099765 A1 | 12/2002 |
| WO | 2005038693 A1 | 4/2005 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007070266 A1 | 6/2007 |
| WO | 2007098762 A1 | 9/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009107011 A1 | 9/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2012084987 A2 | 6/2012 |
| WO | 2013013197 A1 | 1/2013 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2015187366 A1 | 12/2015 |
| WO | 2016132738 A1 | 8/2016 |
| WO | 2016166731 A1 | 10/2016 |
| WO | 2016192738 A1 | 12/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017074505 A1 | 5/2017 |
| WO | 2017088153 A1 | 6/2017 |

(56) References Cited

FOREIGN PATENT DOCUMENTS

| | | |
|---|---|---|
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019120432 A1 | 6/2019 |
| WO | 2019161859 A1 | 8/2019 |
| WO | 2019161860 A1 | 8/2019 |
| WO | 2019161863 A1 | 8/2019 |
| WO | 2019174693 A1 | 9/2019 |
| WO | 2019174695 A1 | 9/2019 |
| WO | 2019213623 A1 | 11/2019 |
| WO | 2020035121 A1 | 2/2020 |

\* cited by examiner

ACCESSORY DEVICES OF A MEDICAL SYSTEM, AND RELATED METHODS FOR COMMUNICATING LEAKAGE STATE

The present disclosure relates to an accessory device of an ostomy system and related methods for monitoring an ostomy appliance. The ostomy appliance system comprises an ostomy appliance, an accessory device and a monitor device. In particular, the present disclosure relates to methods for communicating the leakage state of the ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
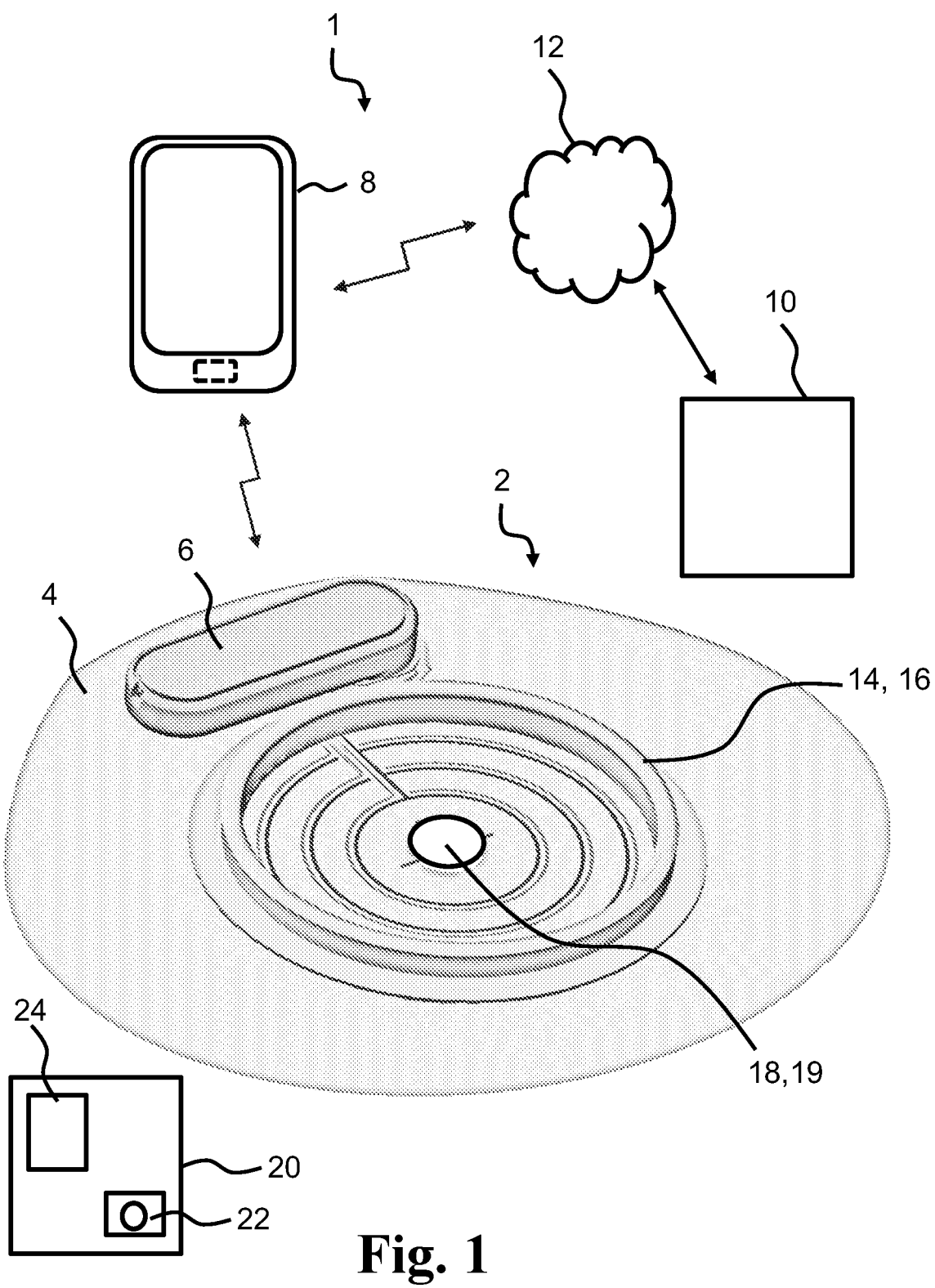
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to an accessory device of the ostomy system and accessory devices thereof are disclosed. An accessory device (also referred to as an external device) may be a mobile phone or other handheld device. An accessory device may be a personal electronic device, e.g. a wearable, such as a watch or other wrist-worn electronic device. The ostomy system may comprise a docking station. An accessory device may be a docking station. An accessory device may act as a docking station. The docking station may be configured to electrically and/or mechanically couple the monitor device to the docking station. The docking station may be configured for charging the monitor device and/or configured for transferring data between the monitor device and the docking station, and/or between the accessory device and the docking station and/or between the monitor device and the accessory device via the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive material, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate comprises a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening with a center point. A base plate with three electrodes having sensing parts with contact to the first adhesive layer allows for determining erosion/swelling properties or characteristics of the first adhesive layer and/or determining a degree of erosion and/or swelling of the first adhesive layer.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance.

Further, determination of operating state and classification of operating states of the ostomy appliance is useful in helping to reduce the risk of a user experiencing leakage from an ostomy appliance. Further, determination of operating state and classification of operating states of the ostomy appliance is further useful in helping reduce the risk of skin damage to a user. In particular, determination of operating state according to the present disclosure may help provide a clear distinction or differentiation between adhesive failure, leakage of output, which is harmful to the skin, and a sweating ostomate.

The present disclosure provides a simple, efficient, and easy-to-use ostomy appliance system with a high degree of comfort for a user The first adhesive layer may be made of a first composition. The first composition may comprise one or more polyisobutenes and/or styrene-isoprene-styrene. The first composition may comprise one or more hydrocoloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocoloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer.

Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate/electrode assembly. The first intermediate element may be arranged between the terminal elements and the first adhesive layer. The first intermediate element may cover or overlap terminal element (s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate coupled to the first interface. The ostomy data may comprise one or more, such as all, of first ostomy data from a first electrode pair of the base plate, second ostomy data from a second electrode pair of the base plate, and third ostomy data from a third electrode pair of the base plate. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by or at least comprise $(P\_1\_1 < TH\_1\_1)$, $(P\_2\_1 > TH\_1\_2)$, and $(P\_3\_1 > TH\_1\_3)$, wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate. The first threshold values (TH_1_1, TH_1_2 and TH_1_3) may be the same or different, e.g. depending on the electrode configuration of the base plate. The first tertiary criterion (P_3_1<TH_1_3) may be omitted in the first criteria set. The first operating state, e.g. indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

In one or more exemplary embodiments, when the first parameter data, the second parameter data and the third parameter data are each respectively indicative of resistance between the first electrode pair, the second electrode pair and the third electrode pair respectively, the first threshold values (TH_1_1, TH_1_2 and TH_1_3) may correspond to first resistance threshold values. In one or more exemplary embodiments, the first primary threshold value TH_1_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the first secondary threshold value TH_1_2 may correspond to the upper resistance threshold value. In one or more exemplary embodiments, the first tertiary threshold value TH_1_3 may correspond to the upper resistance threshold value.

The first primary parameter P_1_1 may be indicative of the resistance between the first electrode pair (first electrode and first electrode part of the ground electrode) of the base plate. The first parameter data may comprise a first secondary parameter which may be derived from the first primary parameter, and/or a first tertiary parameter, which may be derived from the first primary parameter. A first secondary parameter P_1_2 may comprise or be a gradient derived from the first primary parameter. In one or more embodiments, a first primary parameter P_1_1 may be indicative of a voltage between the first electrode pair (first electrode and first electrode part of the ground electrode) of the base plate.

In one or more exemplary embodiments, when the first parameter data, the second parameter data and the third parameter data are each respectively indicative of voltage between the first electrode pair, the second electrode pair and the third electrode pair respectively, the first threshold values (TH_1_1, TH_1_2 and TH_1_3) may correspond to first voltage threshold values. In one or more exemplary embodiments, the first primary threshold value TH_1_1 may correspond to an upper voltage threshold value. An upper voltage threshold value may be set to a value less than 5 Volts, such as 3 Volts, such as 2.86 Volts. In one or more exemplary embodiments, the first secondary threshold value TH_1_2 may correspond to the upper voltage threshold value. In one or more exemplary embodiments, the first tertiary threshold value TH_1_3 may correspond to the upper voltage threshold value.

The first criteria set may comprise e.g.

$(P\_4\_1 > TH\_1\_4)$ wherein P_4_1 is a fourth primary parameter based on the fourth parameter data and indicative of the resistance, voltage, or current between the fourth electrode pair and TH_1_4 is a first quaternary threshold value, and wherein the first operating state is indicative of absence of fluid on the proximal side of the first adhesive layer of the base plate of the ostomy appliance. In one or more exemplary embodiments, the first quaternary threshold value TH_1_4 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the following additional criterion may be determined $(P\_1\_1 < TH\_\text{low})$, wherein P_1_1 is a first primary parameter based on the first parameter data, TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the first electrode pair by the moisture detected and there are no further changes expected by the first primary parameter. Moisture is likely to continue its progression.

In one or more exemplary embodiments, the following additional criterion may be determined $(P\_2\_1 < TH\_\text{low})$, wherein P_2_1 is a second primary parameter based on the second parameter data, TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the second electrode pair by the moisture detected and there are no further changes expected by the second primary parameter. Moisture is likely to continue its progression.

In one or more exemplary embodiments, the following additional criterion may be determined:

$(P\_3\_1 > TH\_\text{low})$,

P_3_1 is a third primary parameter based on the third parameter data, and TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the third electrode pair by the moisture detected and there are no further changes expected by the second primary parameter. Moisture is likely to continue its progression.

In one or more exemplary embodiments, one or more criteria of a criteria set, e.g. one or more first criteria of the first criteria set and/or one or more second criteria of the second criteria set, may be based on timing information or one or more delay parameters based on the parameter data. In one or more exemplary embodiments, one or more delay parameters or time differences related to different parameter data, e.g. related to the first parameter data and the second parameter data, are determined.

In one or more exemplary embodiments, one or more first criteria of the first criteria set may be based on timing information (e.g. one or more delay parameters of the parameter data and/or one or more times where a parameter crosses a threshold).

In one or more exemplary embodiments, the timing information may comprise a time difference $D\_1\_2\_1$ between a time T1 where $P\_1\_1$ crosses a threshold, such as $TH\_1\_1$, and a time T2 where $P\_2\_1$ crosses a threshold, such as $TH\_1\_2$. Thus, delay parameter or time difference $D\_1\_2\_1$ may be given as $D\_1\_2\_1=T2\_T1$.

In one or more exemplary embodiments, the timing information, e.g. used in the first criteria set, may comprise a time difference $D\_2\_3\_1$ between a time T2 where $P\_2\_1$ crosses a threshold, such as $TH\_1\_2$, and a time T3 where $P\_3\_1$ crosses a threshold, such as $TH\_1\_3$. Thus, delay parameter or time difference $D\_2\_3\_1$ may be given as $D\_2\_3\_1=T3\_T2$.

In one or more exemplary embodiments, one or more criteria sets, such as the third criteria set and/or the second criteria set, may comprise any of:

$$D\_1\_2\_1 > Z$$

$$D\_2\_3\_1 > Z$$

Wherein Z is a time difference constant characterizing the progression of moisture (e.g. 3 h, e.g. 2 h). Different time difference constants may be employed in different criteria sets/for different time delays.

In one or more exemplary embodiments, one or more criteria sets, such as the second criteria set and/or the third criteria set may comprise any of:

$$D\_1\_2\_1 > Z$$

Wherein Z is a time difference constant characterizing the progression of moisture (e.g. 3 h, e.g. 2 h).

The second primary parameter may be indicative of the resistance between the second electrode pair (second electrode and second electrode part of the ground electrode) of the base plate. The second parameter data may comprise a second secondary parameter, and/or a second tertiary parameter, which may be derived from the second primary parameter. A second secondary parameter may be indicative of a voltage between the second electrode pair (second electrode and second electrode part of the ground electrode) of the base plate.

The third primary parameter may be indicative of resistance between the third electrode pair (third electrode and third electrode part of the ground electrode) of the base plate. The third parameter data may comprise a third secondary parameter, and/or a third tertiary parameter, which may be derived from the third primary parameter. A third secondary parameter may be indicative of a voltage between the second electrode pair (second electrode and second electrode part of the ground electrode) of the base plate.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by or at least comprise $$(P\_1\_1 < TH\_2\_1),$$

$$(P\_2\_1 < TH\_2\_2), \text{ and}$$

$$(P\_3\_1 > TH\_2\_3)$$

wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate. The second threshold values ($TH\_2\_1$, $TH\_2\_2$ and $TH\_2\_3$) may be the same or different, e.g. depending on the electrode configuration of the base plate. The second primary criterion ($P\_1\_1 < TH\_2\_1$) and/or the second tertiary criterion ($P\_3\_1 > TH\_2\_3$) may be omitted in the second criteria set. The second operating state indicative of medium degree of radial erosion on the base plate may be indicative of a radial progression of moisture to the first electrode pair and the second electrode pair (and not the third electrode pair). The second operating state indicative of medium degree of radial erosion on the base plate may be indicative of a radial progression of moisture to the first electrode pair and to the second electrode pair.

In one or more exemplary embodiments, when the first parameter data, the second parameter data and the third parameter data are each respectively indicative of resistance between the first electrode pair, the second electrode pair and the third electrode pair respectively, the second threshold values ($TH\_2\_1$, $TH\_2\_2$ and $TH\_2\_3$) may correspond to second resistance threshold values. In one or more exemplary embodiments, the second primary threshold value $TH\_2\_1$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the second secondary threshold value TH_2_2 may correspond to the upper resistance threshold. In one or more exemplary embodiments, the second tertiary threshold value TH_2_3 may correspond to the upper resistance threshold value. In one or more exemplary embodiments, the second primary threshold value TH_2_1 may correspond to a medium resistance threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, when the first parameter data, the second parameter data and the third parameter data are each respectively indicative of voltage between the first electrode pair, the second electrode pair and the third electrode pair respectively, the second threshold values (TH_2_1, TH_2_2 and TH_2_3) may correspond to second voltage threshold values. In one or more exemplary embodiments, the second primary threshold value TH_2_1 may correspond to an upper voltage threshold value. An upper voltage threshold value may be set to a value less than 5 Volts, such as 3 Volts, such as 2.86 Volts. In one or more exemplary embodiments, the second secondary threshold value TH_2_2 may correspond to the upper voltage threshold value. In one or more exemplary embodiments, the second tertiary threshold value TH_2_3 may correspond to the upper voltage threshold value. In one or more exemplary embodiments, the second primary threshold value TH_2_1 may correspond to a medium voltage threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, the second criteria set may comprise any of:

$D\_1\_2\_1 > Z$

Wherein Z is a time difference constant characterizing the progression of moisture (e.g. 3 h, e.g. 2 h).

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by or at least comprise $(P\_1\_1 > TH\_D\_1)$, $(P\_2\_1 > TH\_D\_2)$, and $(P\_3\_1 > TH\_D\_3)$ wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate. In one or more exemplary embodiments, when the first parameter data, the second parameter data and the third parameter data are each respectively indicative of resistance between the first electrode pair, the second electrode pair and the third electrode pair respectively, the default threshold values (TH_D_1, TH_D_2 and TH_D_3) may correspond to default resistance threshold values. In one or more exemplary embodiments, the second primary threshold value TH_D_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the default secondary threshold value TH_D_2 may correspond to the upper resistance threshold. In one or more exemplary embodiments, the default tertiary threshold value TH_D_3 may correspond to the upper resistance threshold value.

In one or more exemplary embodiments, when the first parameter data, the second parameter data and the third parameter data are each respectively indicative of voltage between the first electrode pair, the second electrode pair and the third electrode pair respectively, the default threshold values (TH_D_1, TH_D_2 and TH_D_3) may correspond to default voltage threshold values. In one or more exemplary embodiments, the default primary threshold value TH_D_1 may correspond to an upper voltage threshold value. An upper voltage threshold value may be set to a value less than 5 Volts, such as 3 Volts, such as 2.86 Volts. In one or more exemplary embodiments, the default secondary threshold value TH_D_2 may correspond to the upper voltage threshold value. In one or more exemplary embodiments, the default tertiary threshold value TH_D_3 may correspond to the upper voltage threshold value.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate has experienced a third degree of radial erosion, e.g. the first adhesive layer is eroded to the third radial distance of the third electrode pair.

The third criteria set may be given by or at least comprise $(P\_1\_1 < TH\_3\_1)$, $(P\_2\_1 < TH\_3\_2)$, and $(P\_3\_1 < TH\_3\_3)$ wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate. The third threshold values ($TH\_3\_1$, $TH\_3\_2$ and $TH\_3\_3$) may be the same or different, e.g. depending on the electrode configuration of the base plate. The third primary criterion ($P\_1\_1 < TH\_3\_1$) and/or the third secondary criterion ($P\_2\_1 < TH\_3\_2$) may be omitted in the third criteria set. The third operating state indicative of high degree of radial erosion on the base plate may be indicative of high likelihood of leakage, e.g. on the proximal side of the base plate, e.g. within a time period e.g. within the next 20 minutes. The third operating state may indicate a radial progression of moisture to the first electrode pair, the second electrode pair, and the third electrode pair.

In one or more exemplary embodiments, when the first parameter data, the second parameter data and the third parameter data are each respectively indicative of resistance between the first electrode pair, the second electrode pair and the third electrode pair respectively, the third threshold values ($TH\_3\_1$, $TH\_3\_2$ and $TH\_3\_3$) may correspond to third resistance threshold values. In one or more exemplary embodiments, the third primary threshold value $TH\_3\_1$ may correspond to an upper resistance threshold value. In one or more exemplary embodiments, the third secondary threshold value $TH\_3\_2$ may correspond to an upper resistance threshold value. In one or more exemplary embodiments, the third tertiary threshold value $TH\_3\_3$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the third primary threshold value $TH\_3\_1$ may correspond to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. In one or more exemplary embodiments, the third secondary threshold value $TH\_3\_2$ may correspond to a medium resistance threshold. A medium resistance threshold value may be set to a value less than 10 Mega-Ohms, such as 5 Mega-Ohms, such as 3 Mega-Ohms, such as 2 Mega-Ohms, such as 1 Mega-Ohms. In one or more exemplary embodiments, the third tertiary threshold value $TH\_3\_3$ may correspond to the upper resistance threshold. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, when the first parameter data, the second parameter data and the third parameter data are each respectively indicative of voltage between the first electrode pair, the second electrode pair and the third electrode pair respectively, the third threshold values ($TH\_3\_1$, $TH\_3\_2$ and $TH\_3\_3$) may correspond to third voltage threshold values. In one or more exemplary embodiments, the third primary threshold value $TH\_3\_1$ may correspond to an upper voltage threshold value. In one or more exemplary embodiments, the third secondary threshold value $TH\_3\_2$ may correspond to an upper voltage threshold value. In one or more exemplary embodiments, the second tertiary threshold value $TH\_2\_3$ may correspond to the upper voltage threshold value.

In one or more exemplary embodiments, the third primary threshold value $TH\_3\_1$ may correspond to a lower voltage threshold value. In one or more exemplary embodiments, a lower voltage threshold value may be set to a value which is less than 1 Volt, such as 0.5 Volt, such as 0.25 Volts, such as 0.22 Volts. In one or more exemplary embodiments, the third secondary threshold value $TH\_3\_2$ may correspond to a medium voltage threshold value. A medium voltage threshold value may be set to a value less than 2 Volts, such as 1.5 Volts. In one or more exemplary embodiments, the second tertiary threshold value $TH\_2\_3$ may correspond to the upper voltage threshold value.

In one or more exemplary embodiments, one or more third criteria of the third criteria set may comprise any of:

$D\_1\_2\_1 < Z$ $D\_2\_3\_1 < Z$

Wherein Z is a time difference constant characterizing the progression of moisture (e.g. 3 h, e.g. 2 h), a time difference $D\_1\_2\_1$ between a time T1 where $P\_1\_1$ crosses $TH\_1\_1$ and a time T2 where $P\_2\_1$ crosses $TH\_1\_2$, and a time difference $D\_2\_3\_1$ between a time T2 where $P\_2\_1$ crosses $TH\_1\_2$ and a time T3 where $P\_3\_1$ crosses $TH\_1\_3$.

In one or more exemplary monitor devices, the ostomy data comprises fourth ostomy data from a fourth electrode pair of the base plate. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the proximal surface of first adhesive layer and the skin of the user at a fourth radial distance, and thus there is a high risk of leakage from the ostomy appliance in the fourth operating state.

The fourth criteria set may be given by or at least comprise $(P\_4\_1 < TH\_4\_4)$ wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance. In one or more exemplary embodiments, the fourth quaternary threshold value $TH\_4\_4$ may correspond to an upper resistance threshold value.

In one or more exemplary monitor devices, the fifth operating state of the base plate corresponds to a situation, wherein the fourth electrode pair detects fluid, such as sweat, between the proximal surface of first adhesive layer and the skin of the user at a fourth radial distance, and thus there is a no leakage from the ostomy appliance in the fifth operating state.

The fifth operating state may be determined in accordance with a determination that one or more fifth criterion of a fifth criteria set are satisfied.

The fifth criteria set may be given by or at least comprise:

$(P\_4\_1 < TH\_5\_1)$ $(P\_4\_2 < TH\_5\_2)$ $(P\_4\_3 < TH\_5\_3)$ $(\nabla P\_4\_1 < V)$ $(\nabla P\_4\_2 < V)$ $(\nabla P\_4\_3 < V)$ Wherein P_4_1 P_4_1 is a fourth primary parameter based on the fourth parameter data and indicative of the resistance between the fourth electrode pair, P_4_2 is a fourth secondary parameter based on the fourth parameter data and indicative of the resistance between the fourth electrode and the fifth electrode, P_4_3 is a fourth tertiary parameter based on the fourth parameter data and indicative of the resistance between the fifth electrode pair and TH_5_1 is a fifth primary threshold value, TH_5_2 is a fifth secondary threshold value TH_5_3 is a fifth tertiary threshold value and $\nabla P\_4\_1$ is gradient of P_4_1, $\nabla P\_4\_2$ is gradient of P_4_2, $\nabla P\_4\_3$ is gradient of P_4_3, and V is a gradient limit (e.g. 80%). In one or more exemplary embodiments, the fifth primary threshold value TH_5_1 may correspond to an upper resistance threshold value. In one or more exemplary embodiments, TH_5_2 may correspond to an upper resistance threshold value. In one or more exemplary embodiments, TH_5_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The fifth operating state may refer to presence of sweat detected by the fourth parameter data indicating moisture detected omnidirectionally from the stomal opening and uniformly. In one or more exemplary monitor devices, the sixth operating state of the base plate corresponds to a situation, wherein the fourth electrode pair detects fluid, such as output, between the proximal surface of first adhesive layer and the skin of the user at a fourth radial distance, and thus there is a sudden leakage from the ostomy appliance in the sixth operating state.

The sixth operating state may be determined in accordance with a determination that one or more sixth criterion of a sixth criteria set are satisfied.

The sixth criteria set may be given by or at least comprise:

(P_4_1<TH_6_1)

(P_4_2<TH_6_2)

(P_4_3<TH_6_3)

($\nabla P\_4\_1$>V)

($\nabla P\_4\_2$>V)

($\nabla P\_4\_3$>V)

Wherein P_4_1 is a fourth primary parameter based on the fourth parameter data and indicative of the resistance between the fourth electrode pair, P_4_2 is a fourth secondary parameter based on the fourth parameter data and indicative of the resistance between the fourth electrode and the fifth electrode, P_4_3 is a fourth tertiary parameter based on the fourth parameter data and indicative of the resistance between the fifth electrode pair and TH_6_1 is a sixth primary threshold value, TH_6_2 is a sixth secondary threshold value TH_6_3 is a sixth tertiary threshold value, and $\nabla P\_4\_1$ is gradient of P_4_1, $\nabla P\_4\_2$ is gradient of P_4_2, $\nabla P\_4\_3$ is gradient of P_4_3, and V is a gradient limit (e.g. 80%). In one or more exemplary embodiments, the fifth primary threshold value TH_5_1 may correspond to an upper resistance threshold value. In one or more exemplary embodiments, TH_5_2 may correspond to an upper resistance threshold value. In one or more exemplary embodiments, TH_5_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The sixth operating state may refer to presence of output detected by the fourth parameter data indicating a sudden leak, e.g. a developing leak. In one or more exemplary embodiments, when the time T is below X minutes from the placement of the base plate, where X is between 5 to 60 minutes, and when any of P_1_1, P_2_1, P_3_1 in average over T are below a default threshold value corresponding to an upper resistance threshold value, this indicates that any of the first electrode pair, the second electrode pair, and the third electrode pair is cut (e.g. cut by the user when preparing the base plate for placement around the stoma). In one or more exemplary embodiments, when the time T is below X minutes from the placement of the base plate, where X is between 5 to 60 minutes, and when any of P_4_1, P_4_2, P_4_3 in average over T are below a default threshold value corresponding to an upper resistance threshold value, this indicates an instant leakage, e.g. presence of output on the proximal side.

In one or more exemplary embodiments, any of the first criteria set, the second criteria set, the third criteria set, the fourth criteria set, the default criteria set, the fifth criteria set, the sixth criteria set may be used to define one or more further criteria sets, and thereby to determine one or more operating states.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate of the ostomy appliance.

The ostomy system may comprise a docking station forming an accessory device of the ostomy system and/or in addition to the accessory device. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The present disclosure provides a method, performed in an accessory device, for communicating the leakage state of the ostomy appliance, which in turn enables a monitoring of the ostomy appliance at the accessory device. The accessory device comprises an interface configured to communicate with one or more devices of an ostomy system. The one or more devices comprise a monitor device, and/or the ostomy appliance configured to be placed on a skin surface of a user or on any additional seals. The method comprises obtaining (e.g. receiving and/or retrieving) monitor data from the one or more devices. The monitor data is indicative of presence of fluid at a proximal side of the first adhesive layer of the ostomy appliance, towards the skin surface. In one or more exemplary methods, the method comprises determining a leakage state at the proximal side of the first adhesive layer of the ostomy appliance based on the monitor data, and communicating the leakage state of the ostomy appliance via the interface. In other words, the monitor data can be seen as indicative of a moisture condition at a proximal side (or proximal surface) of the first adhesive layer of the ostomy appliance. The presence of fluid at the proximal side (or proximal surface) of the first adhesive layer of the ostomy appliance may be derived at the accessory device based on monitor data.

In one or more exemplary methods, the method may comprise determining a leakage state of the ostomy appliance based on the monitor data obtained. The leakage state may be indicative of presence of output (e.g. feces) at the proximal side or surface of the first adhesive layer of the ostomy appliance. A leakage state in the present disclosure may be indicative of the dynamic internal state of the ostomy appliance, related to the leakage of output (e.g. faecal material, partial leakage or full leakage), such as severity, imminence, timing of leakage at a proximal side (or proximal surface) of the ostomy appliance. By identifying early the presence of fluid, and determining a leakage state as disclosed herein, the likelihood of ending in a situation where output has reached beyond the proximal side (or proximal surface), e.g. out to the clothes of the user, is significantly reduced. Such situation is extremely difficult for the user of the ostomy appliance, due to hygiene and social acceptance.

Presence of fluid on the proximal side (or proximal surface) of the first adhesive layer may affect the adhesive performance of the ostomy appliance. Presence of output on the proximal side of the first adhesive layer affects wear property, e.g. wear time and/or wear comfort of the ostomy appliance.

A leakage state in the present disclosure may be configured to indicate of whether the ostomy appliance needs to be changed immediately based on presence of fluid at a proximal side (or proximal surface) of a first adhesive layer of the ostomy appliance. For example, the leakage state may be indicative of high risk of output going beyond the proximal side (or proximal surface) depending on a corresponding moisture pattern type. For example, the leakage state may be indicative of one or more of severity, imminence of a severe leakage beyond base plate surface, location, timing of the leakage. For example, the leakage state may be indicative of the severity (e.g. no leakage, low, medium, high) and/or imminence of the required change (e.g. no leakage, low, medium, acute). The leakage state may comprise N leakage states, where N is an integer, e.g. for N sensing zones or zones of the base plate. The leakage state may comprise a first leakage state indicative of leakage in a primary sensing zone or in a first zone. The first leakage state may comprise a first primary leakage state, a first secondary leakage state, a first tertiary leakage state, and/or a first quaternary leakage state (e.g. change NOW, check, change in X time, no leakage).

The method comprises communicating (e.g. outputting, transmitting, displaying) the leakage state of the ostomy appliance via the interface, e.g. to the user and/or the one or more devices of the ostomy system.

It is an advantage of the present disclosure that a user of an ostomy appliance or a health care professional is able to be advised on the leakage state of the ostomy appliance and plan the change of the ostomy appliance. Communication of the leakage states of the ostomy appliance is useful in helping to reduce the risk of a user experiencing leakage from an ostomy appliance (e.g. faecal material leakage from the ostomy appliance), which stays long on the skin and increases risks of skin damage to a user (due to e.g. malfunctions and misplacement of the ostomy appliance on the stoma). In particular, determination and communication of leakage state according to the present disclosure is performed based on monitor data indicative of a presence of fluid at the proximal side (or proximal surface) of the ostomy appliance which is not be visible to the user (because it is under the base plate of the ostomy appliance) when the ostomy appliance is worn. This results in providing a clear improvement of the comfort provided by the ostomy appliance in that leakage (incl. partial leakage) of faecal material, which is harmful to the skin is immediately communicated to the user via the accessory device and thereby allowing for a change to happen as soon as possible.

The present disclosure provides an efficient, and easy-to-use communication of a leakage state of an ostomy appliance system with a high degree of comfort for a user. The present disclosure allows to derive and instantly (e.g. substantially in real time) communicate the leakage state based on monitor data that is not accessible or visible by the user or the health care professional. In other words, the disclosed method allows to indicate the dynamic internal state of the ostomy appliance to a user, which results in preventing situations where leakage reached out to the clothes of the user and noticeable for others in the vicinity and eventually improving the life of the ostomate.

In one or more exemplary methods, the ostomy appliance comprises an ostomy pouch and a base plate. In one or more exemplary methods, the base plate comprises a first adhesive layer having a proximal side (or proximal surface). During use, a proximal surface at the proximal side of the first adhesive layer adheres to the user's skin in the peristomal area and/or to additional seals, such as sealing paste, sealing tape and/or sealing ring. In one or more exemplary methods, obtaining the monitor data comprises obtaining the monitor data indicative of the presence of fluid at the proximal side of a first adhesive layer of the base plate. The presence of fluid creates a conductive path at the proximal side of the first adhesive layer, such as on the proximal surface of the first adhesive layer.

In one or more exemplary methods, the base plate comprises a plurality of electrodes configured to detect presence of fluid on the proximal side (or proximal surface) in a primary sensing zone (and/or in a first zone) and a secondary sensing zone (and/or in a second zone). The plurality of electrodes may include a first leakage electrode, a second leakage electrode, and a third leakage electrode. The first leakage electrode may serve as a ground electrode. The second leakage electrode may serve as the fourth electrode of the base plate embodiment disclosed herein. The third leakage electrode may serve as the fifth electrode of the base plate embodiment disclosed herein. Obtaining monitor data may comprise obtaining data representative of detection of fluid on the proximal side (or proximal surface) in the primary sensing zone and the secondary sensing zone. The first adhesive layer may have a stomal opening with a center point. The primary sensing zone may be arranged in a primary angle space from the center point of the first adhesive layer and the secondary sensing zone may be arranged in a secondary angle space from the center point of the first adhesive layer. The primary angle space may span a primary angle in the range from 45° to 315°. The secondary angle space may span a secondary angle in the range from 45° to 315°. The primary sensing zone and the secondary sensing zone may be separate sensing zones, such as non-overlapping sensing zones. The first leakage electrode may comprise one or more primary first sensing parts arranged in the primary sensing zone. The second leakage electrode may comprise one or more primary second sensing parts arranged in the primary sensing zone. The second leakage electrode may comprise one or more secondary second sensing parts arranged in the secondary sensing zone. The third leakage electrode may comprise one or more secondary third sensing parts arranged in the secondary sensing zone.

In one or more exemplary methods, the plurality of electrodes may be configured to detect presence of fluid output on the proximal side in a tertiary sensing zone, the tertiary sensing zone arranged in a tertiary angle space from the center point of the first adhesive layer. The tertiary angle space may span a tertiary angle in the range from 45° to 180°. The primary sensing zone and the tertiary sensing zone may be separate sensing zones. The first leakage electrode may comprise one or more tertiary first sensing parts arranged in the tertiary sensing zone. The third leakage electrode may comprise one or more tertiary third sensing parts arranged in the tertiary sensing zone.

In one or more exemplary methods, the plurality of electrodes of the base plate comprises a ground electrode, a first electrode, a second electrode, and a third electrode, wherein the plurality of electrodes is configured to detect presence of fluid on the proximal side in a first zone, a second zone, a third zone of the base plate. The first zone may be at a first radial distance from a center point of a stomal opening of the base plate. The second zone may be at a second radial distance from the center point of the stomal opening of the base plate. The third zone may be at a third radial distance from the center point of the stomal opening of the base plate. In one or more exemplary methods, the localized monitor data may be with respect to a first zone, a second zone, and/or a third zone.

In one or more exemplary methods, the plurality of electrodes may include a first leakage electrode, a second leakage electrode, a third leakage electrode, a ground electrode, a first electrode, a second electrode, and/or a third electrode, any electrode with the ground electrode may be considered to form a sensor. For example, the monitor data may comprise a first parameter data indicative of resistance between electrodes of a first sensor, a second parameter data indicative of resistance between electrodes of a second sensor, and/or a third parameter data indicative of resistance between electrodes of a third sensor. There may be a fourth parameter data indicative of resistance between electrodes of a fourth sensor.

Full leakage may correspond to a situation where output covers the proximal surface of the first adhesive layer, e.g.

where output is detected by the plurality of electrodes of the base plate. Partial leakage may correspond to a situation where output covers partially the proximal surface of the first adhesive layer, e.g. where output is detected by a part of the plurality of electrodes of the base plate.

In one or more exemplary methods, the monitor data comprises ostomy data and/or parameter data. For example, the parameter data is derived based on ostomy data. Ostomy data or parameter data based on the ostomy data are obtained from electrodes/sensors of the ostomy appliance with e.g. a monitor device or an accessory device. The monitor device may be configured to process the ostomy data and/or parameter data based on the ostomy data to determine monitor data that are transmitted to the accessory device.

In one or more exemplary methods, a plurality of electrodes configured to detect presence of fluid on the proximal side in a primary sensing zone (and/or first zone) and a secondary sensing zone (and/or second zone) by measuring electrical properties of the first adhesive layer. The electrical properties may be indicative of a conductive path in the first adhesive layer, thereby indicative of the presence of fluid at the proximal side of the first adhesive layer of the ostomy appliance. In one or more exemplary methods, obtaining monitor data comprises obtaining data representative of the measurements of the electrical properties at the proximal side of the first adhesive layer. In one or more exemplary methods, the ostomy data and/or parameter data are indicative of resistance between any two of the plurality of electrodes, capacitance and/or inductance between any two of the plurality of electrodes and/or any change thereof. In one or more exemplary methods, the ostomy data and/or parameter data are indicative of a change in resistance, capacitance and/or inductance between electrodes. In one or more exemplary methods, the ostomy data and/or parameter data comprises timing information, such as timestamped data or information from which timing is derivable.

In one or more exemplary methods, the monitor data comprises localized monitor data with respect to a location and/or a zone at the proximal side of the first adhesive layer of the base plate. Determining the leakage state may comprise determining a leakage location and/or a leakage time information. The location and/or region at the proximal side of the first adhesive layer of the base place may be related to a position at the proximal side of the first adhesive layer where electrical properties have been measured by the one or more electrodes. In one or more exemplary methods, obtaining the monitor data comprises obtaining (e.g. receiving from one or more devices in the ostomy system, and/or retrieving from one or more devices in the ostomy system) localized monitor data with respect to a location and/or zone at the proximal side of the first adhesive layer of the base plate. In one or more exemplary methods, the localized monitor data may be with respect to a first location, a second location, a third location. In one or more exemplary methods, the localized monitor data may be with respect to a first zone, a second zone, and/or a third zone on proximal side of first adhesive layer of the base plate. The leakage state of the ostomy appliance may be based on the moisture pattern type determined using e.g. parameter data obtained from one or more devices, such as a monitor device coupled with the base plate having e.g. electrodes placed in respective zones of the base plate (such as electrodes of FIG. 6 and/or sensor points openings of FIG. 7).

In one or more exemplary methods, the monitor data may comprise first localized monitor data indicative of presence of fluid at a first location of the proximal side of the first adhesive layer of base plate or at a first zone of the proximal side of the first adhesive layer of base plate, second localized monitor data indicative of presence of fluid at a second location of the proximal side of the first adhesive layer of base plate or at a second zone of the proximal side of the first adhesive layer of base plate. For example, parameter data may comprise first parameter data indicative of the presence of fluid at a first zone and/or a primary sensing zone. For example, parameter data may comprise second parameter data indicative of the presence of fluid at a second zone and/or a secondary sensing zone. For example, parameter data may comprise third parameter data indicative of the presence of fluid at a third zone, and/or a tertiary sensing zone.

In one or more exemplary methods, determining the leakage state of the ostomy appliance based on the monitor data comprises determining one or more moisture pattern types based on the monitor data, such as based on the ostomy data and/or the parameter data (e.g. first parameter data and optionally second parameter data), such as based on measurements obtained by the electrodes, such as measurements of resistance, capacitance and/or inductance, such as timing information, for e.g. a first primary sensing zone (and/or first zone), and optionally a second primary sensing zone (and/or second zone). The moisture pattern type is optionally indicative of leakage risk of the ostomy appliance and/or indicative of the risk of skin damage to the user of the ostomy system. In one or more exemplary methods, determining the leakage state of the ostomy appliance based on the monitor data comprises determining one or more moisture pattern types based on the first parameter data (and optionally second parameter data and optionally a third parameter).

In one or more exemplary methods, determining one or more moisture pattern types may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

In one or more exemplary methods, the method comprises determining whether the leakage state fulfils a leakage criterion indicative of leakage risk (e.g. high risk of a severe leakage), and performing the step of communicating the leakage state when the leakage state fulfils the leakage criterion. The leakage criterion may comprise one or more criteria, such as first criteria, second criteria, third criteria.

In one or more exemplary methods, determining the leakage state of the ostomy appliance based on the monitor data comprises deriving the leakage state based on the one or more moisture pattern types, such as deriving a first leakage state based on a first moisture pattern type, deriving a second leakage state based on a second moisture pattern type, and/or deriving a third leakage state based on a third moisture pattern type.

In one or more exemplary methods, determining one or more moisture pattern types comprises determining whether at least one of the first parameter data, the second parameter data, and optionally the third parameter data meets one or more first criteria in any one or more of the primary, secondary and tertiary sensing zone (and/or any one or more of the first, second, and third zone) respectively, and the moisture pattern type is set to the first moisture pattern type in any one or more of the primary, secondary and tertiary sensing zone (and/or any one or more of the first, second, and third zone) if the first criteria are met for the first parameter data, the second parameter data, and/or the third parameter data respectively. The leakage criterion may comprise first criteria, and when the first criteria are met, the leakage criterion is met. For example, the first criteria may comprise a first primary criterion based on the first parameter data, a first secondary criterion based on the second parameter data, and optionally a first tertiary criterion based on the third parameter data. For example, the first criteria may be given by or at least comprise e.g.:

$$(P\_1\_1 < TH\_1\_1),$$

$$(P\_2\_1 < TH\_1\_2) \text{ and}$$

$$(P\_3\_1 < TH\_1\_3),$$

wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value. The first moisture pattern type may be indicative of a first primary leakage state, which is indicative of high risk (e.g. high severity and/or high imminence) of leakage in the primary sensing zone and/or in the first zone. The first moisture pattern type may be indicative of a second primary leakage state, which is indicative of high risk (e.g. high severity and/or high imminence of highly severe leakage) of leakage in the secondary sensing zone and/or in the second zone. The first moisture pattern type may be indicative of a third primary leakage state, which is indicative of high risk (e.g. high severity and/or high imminence of highly severe leakage) of leakage in the tertiary sensing zone and/or in the third zone. The first operating state indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

In one or more exemplary methods, when the first parameter data, the second parameter data and the third parameter data are each respectively indicative of resistance between the first electrode pair, the second electrode pair and the third electrode pair respectively, the first threshold values (TH_1_1, TH_1_2 and TH_1_3) may correspond to first resistance threshold values. In one or more exemplary embodiments, the first primary threshold value TH_1_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the first secondary threshold value TH_1_2 may correspond to the upper resistance threshold value. In one or more exemplary embodiments, the first tertiary threshold value TH_1_3 may correspond to the upper resistance threshold The first parameter data, the second parameter data, and the third parameter data may be indicative of voltage between the first electrode pair, the second electrode pair, and the third electrode pair, respectively (and thus indicative of resistance). The first parameter data, the second parameter data, and the third parameter data may be indicative of current between the first electrode pair, the second electrode pair, and the third electrode pair, respectively (and thus indicative of resistance).

The first primary parameter P_1_1 may be indicative of the resistance between the first electrode pair (first electrode and first electrode part of the ground electrode) of the base plate. A first secondary parameter P_1_2 may be indicative of rate of change of the first primary parameter.

In one or more exemplary methods, when the first parameter data, the second parameter data and the third parameter data are each respectively indicative of voltage between the first electrode pair, the second electrode pair and the third electrode pair respectively, the first threshold values (TH_1_1, TH_1_2 and TH_1_3) may correspond to first voltage threshold values. In one or more exemplary embodiments, the first primary threshold value TH_1_1 may correspond to an upper voltage threshold value. An upper voltage threshold value may be set to a value less than 5 Volts, such as 3 Volts, such as 2.86 Volts. In one or more exemplary embodiments, the first secondary threshold value TH_1_2 may correspond to the upper voltage threshold value. In one or more exemplary embodiments, the first tertiary threshold value TH_1_3 may correspond to the upper voltage threshold value.

In one or more exemplary methods, the first criteria may comprise e.g.

$$(P\_4\_1 > TH\_4\_4)$$

wherein P_4_1 is a fourth primary parameter based on the fourth parameter data and indicative of the resistance between the fourth electrode pair and TH_4_4 is a fourth quaternary threshold value, and wherein the first operating state is indicative of absence of fluid on the proximal side of the first adhesive layer of the base plate of the ostomy appliance. In one or more exemplary embodiments, the fourth quaternary threshold value TH_4_4 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary methods, the following may be determined to indicate saturation of the first electrode pair by moisture:

$$(P\_1\_1 < TH\_1\_1),$$

wherein P_1_1 is a first primary parameter based on the first parameter data, TH_1_1 is a first primary threshold value. When the first primary threshold value TH_1_1 corresponds to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the first electrode pair by the moisture detected and there are no further changes expected by the first primary parameter. Moisture is likely to continue its progression.

In one or more exemplary methods, the following may be determined to indicate saturation of the second electrode pair by moisture:

$$(P\_2\_1 < TH\_1\_2),$$

wherein P_2_1 is a second primary parameter based on the second parameter data, TH_1_2 is a first secondary threshold value. When the first secondary threshold value TH_1_2 corresponds to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the second electrode pair by the moisture detected and there are no further changes expected by the second primary parameter. Moisture is likely to continue its progression.

In one or more exemplary embodiments, the following may be determined to indicate saturation of the third electrode pair by moisture:

$$(P\_3\_1 > TH\_1\_3),$$

P_3_1 is a third primary parameter based on the third parameter data, and TH_1_3 is a first tertiary threshold value. When the first tertiary threshold value TH_1_3 corresponds to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the third electrode pair by the moisture detected and there are no further changes expected by the second primary parameter. Moisture is likely to continue its progression.

In one or more exemplary methods, the first criteria may be based on timing information (e.g. delay parameters of the parameter data).

In one or more exemplary methods, the timing information may comprise a time difference D_1_2_1 between a time T1 where P_1_1 crosses TH_1_1 and a time T2 where P_2_1 crosses TH_1_2. In one or more exemplary embodiments, the timing information may comprise a time difference D_2_3_1 between a time T2 where P_2_1 crosses TH_1_2 and a time T3 where P_3_1 crosses TH_1_3.

In one or more exemplary methods, the first criteria may comprise any of:

$$D\_1\_2\_1 > Z$$

$$D\_2\_3\_1 > Z$$

Wherein Z is a time difference constant characterizing the progression of moisture (e.g. 3 h, e.g. 2 h).

The second primary parameter may be indicative of the resistance between the second electrode pair (second electrode and second electrode part of the ground electrode) of the base plate. The second parameter data may comprise a second secondary parameter, and/or a second tertiary parameter, which may be derived from the second primary parameter. A second secondary parameter may be indicative of a voltage between the second electrode pair (second electrode and second electrode part of the ground electrode) of the base plate.

The third primary parameter may be indicative of resistance between the third electrode pair (third electrode and third electrode part of the ground electrode) of the base plate. The third parameter data may comprise a third secondary parameter, and/or a third tertiary parameter, which may be derived from the third primary parameter. A third secondary parameter may be indicative of a voltage between the second electrode pair (second electrode and second electrode part of the ground electrode) of the base plate.

In one or more exemplary methods, determining one or more moisture pattern types comprises determining whether at least one of the first parameter data, the second parameter data, and the third parameter data meets one or more second criteria in any one or more of the primary, secondary and tertiary sensing zone (and/or any one or more of the first, second, and third zone) respectively, and the moisture pattern type is set to the second type in any one or more of the primary, secondary and tertiary sensing zone (and/or any one or more of the first, second, and third zone) respectively if the second criteria are met for the corresponding parameter data amongst the first parameter data, the second parameter data, and the third parameter data. For example, the second criteria may be given by or at least comprise e.g.:

$$(P\_1\_1 > TH\_2\_1),$$

$$(P\_2\_1 > TH\_2\_2), \text{ and}$$

$$(P\_3\_1 > TH\_2\_3)$$

wherein P_1_1 is a first primary parameter based on the first parameter data, TH_2_1 is a second primary threshold value, P_2_1 is a second primary parameter based on the second parameter data, TH_2_2 is a second secondary threshold value, P_3_1 is a third primary parameter based on the third parameter data, TH_2_3 is a second tertiary threshold value. The second moisture pattern type may be indicative of a first secondary leakage state, which is indicative of low risk (e.g. low severity and/or low imminence) of leakage in the primary sensing zone and/or first zone. The second moisture pattern type may be indicative of a second secondary leakage state, which is indicative of low risk (e.g. low severity and/or low imminence of highly severe leakage) of leakage in the secondary sensing zone and/or second zone. The second moisture pattern type may be indicative of a third secondary leakage state, which is indicative of low risk (e.g. low severity and/or low imminence of highly severe leakage) of leakage in the tertiary sensing zone and/or in the third zone. The second criteria may be comprised in the leakage criterion wherein when the second criteria are met, the leakage criterion is met. The second operating state indicative of medium degree of radial erosion on the base plate may be indicative of a radial progression of moisture to the first electrode pair and the second electrode pair (and not the third electrode pair). The second operating state indicative of medium degree of radial erosion on the base plate may be indicative of a radial progression of moisture to the first electrode pair and to the second electrode pair.

In one or more exemplary embodiments, when the first parameter data, the second parameter data and the third parameter data are each respectively indicative of resistance between the first electrode pair, the second electrode pair and the third electrode pair respectively, the second threshold values (TH_2_1, TH_2_2 and TH_2_3) may correspond to second resistance threshold values. In one or more exemplary embodiments, the second primary threshold value TH_2_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the second secondary threshold value TH_2_2 may correspond to the upper resistance threshold. In one or more exemplary embodiments, the second tertiary threshold value TH_2_3 may correspond to the upper resistance threshold value. In one or more exemplary embodiments, the second primary threshold value TH_2_1 may correspond to a medium resistance threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, when the first parameter data, the second parameter data and the third parameter data are each respectively indicative of voltage between the first electrode pair, the second electrode pair and the third electrode pair respectively, the second threshold values (TH_2_1, TH_2_2 and TH_2_3) may correspond to second voltage threshold values. In one or more exemplary embodiments, the second primary threshold value TH_2_1 may correspond to an upper voltage threshold value. An upper voltage threshold value may be set to a value less than 5 Volts, such as 3 Volts, such as 2.86 Volts. In one or more exemplary embodiments, the second secondary threshold value TH_2_2 may correspond to the upper voltage threshold value. In one or more exemplary embodiments, the second tertiary threshold value TH_2_3 may correspond to the upper voltage threshold value. In one or more exemplary embodiments, the second primary threshold value TH_2_1 may correspond to a medium voltage threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary methods, determining one or more moisture pattern types comprises determining whether at least one of the first parameter data, the second parameter data, and optionally the third parameter data meets default criteria, and the moisture pattern type is set to the default moisture pattern type if the default criteria is met. The operating state is determined to be the default operating state if the default criteria set is satisfied, and in accordance with a determination that the operating state is the default operating state.

The default criteria may be given by or at least comprise:

$(P\_1\_1 > TH\_D\_1)$, $(P\_2\_1 > TH\_D\_2)$, and $(P\_3\_1 > TH\_D\_3)$ wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate. In one or more exemplary embodiments, when the first parameter data, the second parameter data and the third parameter data are each respectively indicative of resistance between the first electrode pair, the second electrode pair and the third electrode pair respectively, the default threshold values (TH_D_1, TH_D_2 and TH_D_3) may correspond to default resistance threshold values. In one or more exemplary embodiments, the second primary threshold value TH_D_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the default secondary threshold value TH_D_2 may correspond to the upper resistance threshold. In one or more exemplary embodiments, the default tertiary threshold value TH_D_3 may correspond to the upper resistance threshold value.

In one or more exemplary methods, when the first parameter data, the second parameter data and the third parameter data are each respectively indicative of voltage between the first electrode pair, the second electrode pair and the third electrode pair respectively, the default threshold values (TH_D_1, TH_D_2 and TH_D_3) may correspond to default voltage threshold values. In one or more exemplary embodiments, the default primary threshold value TH_D_1 may correspond to an upper voltage threshold value. An upper voltage threshold value may be set to a value less than 5 Volts, such as 3 Volts, such as 2.86 Volts. In one or more exemplary embodiments, the default secondary threshold value TH_D_2 may correspond to the upper voltage threshold value. In one or more exemplary embodiments, the default tertiary threshold value TH_D_3 may correspond to the upper voltage threshold value.

In one or more exemplary methods, determining one or more moisture pattern types comprises determining whether at least one of the first parameter data, the second parameter data, and/or the third parameter data meets one or more third criteria in any one or more of the primary, secondary, and tertiary sensing zone (and/or any one or more of the first, second, and third zone) respectively. The moisture pattern type may be set to the third moisture pattern type in any one or more of the primary, secondary and tertiary sensing zone (and/or any one or more of the first, second, and third zone) if the third criteria are met for the corresponding parameter data amongst the first parameter data, the second parameter data, and the third parameter data. In one or more exemplary methods, the third criteria are given by or at least comprise:

$(P\_1\_1 > TH\_3\_1)$, $(P\_2\_1 > TH\_3\_2)$, and $(P\_3\_1 > TH\_3\_3)$, wherein P_1_1 is a first primary parameter, optionally indicative of resistance between respective electrodes of a first sensor, based on the first parameter data, TH_3_1 is a third primary threshold value, P_2_1 is a second primary parameter, optionally indicative of resistance between respective electrodes of a second sensor, based on the second parameter data, TH_3_2 is a third secondary threshold value, P_3_1 is a third primary parameter, optionally indicative of resistance between respective electrodes of a third sensor, based on the third parameter data, TH_3_3 is a third tertiary threshold value. The third moisture pattern type may be indicative of a first tertiary leakage state, which is indicative of very low risk (e.g. very low severity and/or very low imminence of severe leakage) of leakage in the primary sensing zone and/or the first zone. The third moisture pattern type is indicative of a second tertiary leakage state, which is indicative of very low risk (e.g. very low severity and/or very low imminence of severe leakage) of leakage in the tertiary sensing zone and/or the third zone. The third moisture pattern type may be indicative of a third tertiary leakage state, which is indicative of very low risk (e.g. very low severity and/or very low imminence of severe leakage) of leakage in the tertiary sensing zone and/or the third zone. The third criteria may be comprised in the leakage criterion wherein when the third criteria are met, the leakage criterion is met. The third operating state indicative of high degree of radial erosion on the base plate may be indicative of high likelihood of leakage, e.g. on the proximal side of the base plate, e.g. within a time period e.g. within the next 20 min. The third operating state may indicate a radial progression of moisture to the first electrode pair, the second electrode pair, and the third electrode pair.

In one or more exemplary embodiments, when the first parameter data, the second parameter data and the third parameter data are each respectively indicative of resistance between the first electrode pair, the second electrode pair and the third electrode pair respectively, the third threshold values (TH_3_1, TH_3_2 and TH_3_3) may correspond to third resistance threshold values. In one or more exemplary embodiments, the third primary threshold value TH_3_1 may correspond to an upper resistance threshold value. In one or more exemplary embodiments, the third secondary threshold value TH_3_2 may correspond to an upper resistance threshold value. In one or more exemplary embodiments, the third tertiary threshold value TH_3_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the third primary threshold value TH_3_1 may correspond to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. In one or more exemplary embodiments, the third secondary threshold value TH_3_2 may correspond to a medium resistance threshold. A medium resistance threshold value may be set to a value less than 10 Mega-Ohms, such as 5 Mega-Ohms, such as 3 Mega-Ohms, such as 2 Mega-Ohms, such as 1 Mega-Ohms. In one or more exemplary embodiments, the third tertiary threshold value TH_3_3 may correspond to the upper resistance threshold. An upper resistance threshold value may be set to a value which is less than 30 Mega-Ohms, such as 25 Mega-Ohms, such as 20.5 Mega-Ohms, such as 20.4 Mega-Ohms.

In one or more exemplary methods, when the first parameter data, the second parameter data and the third parameter data are each respectively indicative of voltage between the first electrode pair, the second electrode pair and the third electrode pair respectively, the third threshold values (TH_3_1, TH_3_2 and TH_3_3) may correspond to third voltage threshold values. In one or more exemplary embodiments, the third primary threshold value TH_3_1 may correspond to an upper voltage threshold value. In one or more exemplary embodiments, the third secondary threshold value TH_3_2 may correspond to an upper voltage threshold value. In one or more exemplary embodiments, the second tertiary threshold value TH_2_3 may correspond to the upper voltage threshold value.

In one or more exemplary methods, the third primary threshold value TH_3_1 may correspond to a lower voltage threshold value. In one or more exemplary embodiments, a lower voltage threshold value may be set to a value which is less than 1 Volt, such as 0.5 Volt, such as 0.25 Volts, such as 0.22 Volts. In one or more exemplary embodiments, the third secondary threshold value TH_3_2 may correspond to a medium voltage threshold value. A medium voltage threshold value may be set to a value less than 2 Volts, such as 1.5 Volts. In one or more exemplary embodiments, the second tertiary threshold value TH_2_3 may correspond to the upper voltage threshold value.

In one or more exemplary embodiments, the third criteria set may comprise any of:

$(D\_1\_2\_1 < Z)$ $(D\_2\_3\_1 < Z)$

Wherein Z is a time difference constant characterizing the progression of moisture (e.g. 3 h, e.g. 2 h), a time difference D_1_2_1 between a time T1 where P_1_1 crosses TH_1_1 and a time T2 where P_2_1 crosses TH_1_2, and a time difference D_2_3_1 between a time T2 where P_2_1 crosses TH_1_2 and a time T3 where P_3_1 crosses TH_1_3.

In one or more exemplary methods, a fourth operating state of the base plate corresponds to a situation, wherein the fourth electrode pair detects fluid, such as output, between the proximal surface of first adhesive layer and the skin of the user at a fourth radial distance, and thus there is a high risk of leakage from the ostomy appliance in the fourth operating state.

The fourth criteria set may be given by or at least may comprise:

$(P\_4\_1 < TH\_4\_4)$ wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance. In one or more exemplary embodiments, the fourth quaternary threshold value TH_4_4 may correspond to an upper resistance threshold value.

In one or more exemplary monitor devices, a fifth operating state of the base plate corresponds to a situation, wherein the fourth electrode pair detects fluid, such as sweat, between the proximal surface of first adhesive layer and the skin of the user at a fourth radial distance, and thus there is a no leakage from the ostomy appliance in the fifth operating state.

The fifth operating state may be determined in accordance with a determination that one or more fifth criterion of a fifth criteria set are satisfied.

The fifth criteria set may be given by or at least may comprise:

$(P\_4\_1 < TH\_5\_1)$ $(P\_4\_2 < TH\_5\_2)$ $(P\_4\_3 < TH\_5\_3)$ $(\nabla P\_4\_1 < V)$ $(\nabla P\_4\_2 < V)$ and $(\nabla P\_4\_3 < V)$ Wherein P_4_1 is a fourth primary parameter based on the fourth parameter data and indicative of the resistance between the fourth electrode pair, P_4_2 is a fourth secondary parameter indicative of the resistance between the fourth electrode and the fifth electrode, P_4_3 is a fourth tertiary parameter based on the fourth parameter data and indicative of the resistance between the fifth electrode pair and TH_5_1 is a fifth primary threshold value, TH_5_2 is a fifth secondary threshold value TH_5_3 is a fifth tertiary threshold value and $\nabla P\_4\_1$ is gradient of P_4_1, $\nabla P\_4\_2$ is gradient of P_4_2, $\nabla P\_4\_3$ is gradient of P_4_3, and V is a gradient limit (e.g. 80%). In one or more exemplary embodiments, the fifth primary threshold value TH_5_1 may correspond to an upper resistance threshold value. In one or more exemplary embodiments, TH_5_2 may correspond to an upper resistance threshold value. In one or more exemplary embodiments, TH_5_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The fifth operating state may refer to presence of sweat detected by the fourth parameter data indicating moisture detected omnidirectionally from the stomal opening and uniformly.

In one or more exemplary monitor devices, the sixth operating state of the base plate corresponds to a situation, wherein the fourth electrode pair detects fluid, such as output, between the proximal surface of first adhesive layer and the skin of the user at a fourth radial distance, and thus there is a sudden leakage from the ostomy appliance in the sixth operating state.

A sixth operating state may be determined in accordance with a determination that one or more sixth criteria of a sixth criteria set are satisfied.

The sixth criteria set may comprise a sixth primary criterion, wherein the sixth primary criterion may comprise:

$(P\_4\_1 < TH\_6\_1)$ and $(\nabla P\_4\_1 > V)$

The sixth criteria set may comprise a sixth secondary criterion, wherein the sixth secondary criterion may comprise:

$(P\_4\_2 < TH\_6\_2)$ and $(\nabla P\_4\_2 > V)$

The sixth criteria set may comprise a sixth tertiary criterion, wherein the sixth tertiary criterion may comprise:

$(P\_4\_3 < TH\_6\_3)$ and $(\nabla P\_4\_3 > V)$

Wherein P_4_1 is a fourth primary parameter based on the fourth parameter data and indicative of the resistance between the fourth electrode pair, P_4_2 is a fourth secondary parameter indicative of the resistance between the fourth electrode and the fifth electrode, P_4_3 is a fourth tertiary parameter indicative of the resistance between the fifth electrode pair (fifth electrode and ground electrode) and TH_6_1 is a sixth primary threshold value, TH_6_2 is a sixth secondary threshold value TH_6_3 is a sixth tertiary threshold value, and $\nabla P\_4\_1$ is gradient of P_4_1, $\nabla P\_4\_2$ is gradient of P_4_2, $\nabla P\_4\_3$ is gradient of P_4_3, and V is a gradient limit (e.g. 80%). In one or more exemplary embodiments, the sixth primary threshold value TH_6_1 may correspond to an upper resistance threshold value. In one or more exemplary embodiments, TH_6_2 may correspond to an upper resistance threshold value. In one or more exemplary embodiments, TH_6_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The sixth operating state may refer to presence of output detected by the fourth parameter data indicating a sudden leak, e.g. a developing leak. In one or more exemplary embodiments, when the time T is below X minutes from the placement of the base plate, where X is between 5 to 60 minutes, and when any of P_1_1, P_2_1, P_3_1 in average over T are below a default threshold value corresponding to an upper resistance threshold value, this indicates that any of the first electrode pair, the second electrode pair, and the third electrode pair is cut (e.g. cut by the user when preparing the base plate for placement around the stoma). In one or more exemplary embodiments, when the time T is below X minutes from the placement of the base plate, where X is between 5 to 60 minutes, and when any of P_4_1, P_4_2, P_4_3 in average over T are below a default threshold value corresponding to an upper resistance threshold value, this indicates an instant leakage, e.g. presence of output on the proximal side.

In one or more exemplary embodiments, any of the first criteria set, the second criteria set, the third criteria set, the fourth criteria set, the default criteria set, the fifth criteria set, the sixth criteria set may be used to define one or more further criteria sets, and thereby to determine one or more operating states.

In one or more exemplary embodiments, different criteria sets may be used to determine the same operating state.

Parameter data (e.g. the first parameter data, the second parameter data, the third parameter data) may be indicative of a change in resistance between any two of the plurality of electrodes (wherein at least one electrode acts as a ground electrode), such as a drop or decrease in resistance between the two electrodes, which is indicative of a conductive path between the electrodes created by presence of foreign conductive material, i.e. presence of fluid between the electrodes (i.e. faecal material). The first parameter data may be indicative of a change in resistance between electrodes of the first sensor, such as a drop or decrease in resistance between electrodes of the first sensor, which is indicative of a conductive path between the electrodes created by presence of foreign conductive material, i.e. presence of fluid between the electrodes. The second parameter data may be indicative of a change in resistance between electrodes of the second sensor, such as a drop or decrease in resistance between electrodes of the second sensor, which is indicative of a conductive path between the electrodes created by presence of foreign conductive material, i.e. presence of fluid between the electrodes. The third parameter data may be indicative of a change in resistance between electrodes of the third sensor, such as a drop or decrease in resistance between electrodes of the first sensor, which is indicative of a conductive path between the electrodes created by presence of foreign conductive material, i.e. presence of fluid between the electrodes. The fourth parameter data may be indicative of a change in resistance between electrodes of the fourth sensor, such as a drop or decrease in resistance between electrodes of the fourth sensor, which is indicative of a conductive path between the electrodes created by presence of foreign conductive material, i.e. presence of fluid between the electrodes. In one or more exemplary methods, the method comprises: determining whether the leakage state fulfils a leakage criterion indicative of high risk (risk of skin damage, of leakage beyond the surface of the base plate and into clothes), and performing the step of communicating the leakage state when the leakage state fulfils a leakage criterion.

In one or more exemplary methods, determining one or more moisture pattern types based on the monitor data comprises identifying a moisture pattern type based on parameter data, such as for the corresponding zone, such as first parameter data. In one or more exemplary methods, determining one or more moisture pattern types comprises determining a moisture pattern type if a leakage criterion is fulfilled. The leakage criterion may be based on the first parameter data, the second parameter data and/or the third parameter data. The leakage criterion may be fulfilled if parameter data changes, e.g. if a change in parameter data is larger than a leakage threshold. Thus, the moisture pattern type determination may be conditional on a change in the parameter data, in turn leading to an optimum use of power or battery resources in the ostomy monitor device, and in timely communication to the user via the interface.

In one or more exemplary methods, determining one or more moisture pattern types based on the monitor data comprises comparing first parameter data, second parameter data, and third parameter data. In one or more exemplary methods, determining one or more moisture pattern types based on the monitor data comprises identifying a moisture pattern type based on the comparison. For example, an exemplary criterion, such as one or more of a first criterion (of the first criteria), a second criterion (of the second criteria) and a third criterion (of the third criteria), may be based on a difference and/or deviation rate between parameter data and/or parameters derived from parameter data. For example, determining a moisture pattern comprises determining a first tertiary parameter, also denoted P_1_3, indicative of a time delay between changes in the first parameter data and the second parameter data, such as a time delay between the first parameter data reaching (or being below) a first threshold and the second parameter data reaching (or being below) a second threshold. A high time delay (e.g. leakage criterion: P_1_3>TH_D_1) may be indicative of leakage of faecal material (and thus high risk of skin damage), while a low time delay (P_1_3<TH_D_1) may be indicative of the ostomate perspiring or sweating. One or more criteria may be based on the first tertiary parameter. For example, determining a moisture pattern comprises determining a third tertiary parameter, also denoted P_3_3, indicative of a time delay between changes in the third parameter data and the fourth parameter data, such as a time delay between the third parameter data reaching (or being below) a third threshold and the fourth parameter data reaching (or being below) a fourth threshold. A high time delay (e.g. leakage criterion: P_3_3>TH_D_3) may be indicative of leakage of faecal material (and thus high risk of skin damage), while a low time delay (P_3_3<TH_D_1) may be indicative of the ostomate perspiring or sweating. One or more criteria may be based on the third tertiary parameter.

In one or more exemplary methods, the interface comprises an audio interface, a visual interface, and/or a transceiver module.

A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user, and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the base plate.

In one or more exemplary methods, communicating the leakage state of the ostomy appliance comprises displaying, on a visual interface (e.g. a display) of the accessory device, a user interface comprising a user interface object representative of the leakage state, such as a first user interface object representative of a first leakage state, a second user interface object representative of a second leakage state, and/or a third user interface object representative of a third leakage state. The user interface object may be representative of one or more moisture pattern types determined, such as a first moisture pattern type, a second moisture pattern type, and/or a third moisture pattern type.

In one or more exemplary methods, the user interface object representative of the leakage state comprises one or more of a first user interface object, and a second user interface object, wherein the first and/or second user interface objects are indicative of one or more of a first leakage state, a second leakage state and a third leakage state. For example, the user interface object may comprise one or more visual indicators representative of the leakage state, such as a first visual indicator, a second visual indicator, a third visual indicator. For example, the visual indicator may be in a shape of two or more concentric rings indicating one or more of: the moisture pattern type, severity, imminence, and/position of the presence of fluid in the base plate, such as the moisture pattern type. For example, two or more concentric rings may be arranged to surround a central circle representative of the stomal opening of the base plate. For example, the two or more concentric rings around the central circle may visually change to reflect the moisture pattern type, severity, imminence, and/or position of the presence of fluid in the base plate, such as the moisture pattern type. The visual change may be performed by a change of one or more of: colour, shape, blurring, and animation. For example, the two or more concentric rings may be arranged so as to be split into a plurality of angular visual indicators, wherein an angular visual indicator is indicative of the angular position of the presence of fluid, such as the moisture pattern type on the base plate. For example, the visual indicators may be a text prompt indicating to the user the dynamic internal leakage state of the ostomy appliance.

In one or more exemplary methods, communicating the leakage state of the ostomy appliance comprises notifying the user via the interface, such as by displaying a notification on a display of the accessory device. The notification may comprise the user interface object representative of the leakage state. The notification may comprise a notification indicator to open an application related to the ostomy appliance. The method may comprise detecting an input on the notification indicator, in response to the input, opening the application related to the ostomy appliance, and in response to the opening of the application, displaying the leakage state on the visual interface.

In one or more exemplary methods, the ostomy system comprises a server device. In one or more exemplary methods, communicating the leakage state of the ostomy appliance comprises communicating the leakage state of the ostomy appliance to the server device. For example, communicating the leakage state of the ostomy appliance to the server device may comprise transmitting a message comprising the leakage state to the server device from the accessory device.

The present disclosure provides an accessory device, the accessory device forms part of an ostomy system. The accessory device comprises a memory; a processor coupled to the memory; and an interface, coupled to the processor. The interface is configured to communicate with one or more devices of the ostomy system. The one or more devices comprising a monitor device, and/or an ostomy appliance configured to be placed on a skin surface of a user or on any additional seals. The interface is configured to obtain monitor data from the one or more devices, such as to receive or retrieve the monitor data from the one or more devices. The monitor data may be indicative of a presence of fluid at a proximal side (or proximal surface) of a layer, such as a first adhesive layer of the ostomy appliance that is directed towards the skin surface, such as a first adhesive layer of a base plate of the ostomy appliance.

The processor may be configured to determine a leakage state of the ostomy appliance based on the monitor data obtained. The leakage state may be indicative of the dynamic internal state of the ostomy appliance (for example early presence of fluid that is not visible to the user when the ostomy appliance is worn), related to the leakage of output (e.g. faecal material), such as severity, imminence, timing of leakage at a proximal side of the ostomy appliance. Presence of fluid on the proximal side (or proximal surface) of the first adhesive layer may affect the adhesive performance of the ostomy appliance. The processor may be configured to determine the leakage state by determining a moisture pattern type as provided in the method disclosed herein. The moisture pattern type may be based on one or more, such as all, of first monitor data, second monitor data, and third monitor data, such as first parameter data, second parameter data and the third parameter data. The moisture pattern type may be based on the fourth parameter data. For example, the leakage state is indicative of adhesive failure of the base plate and/or leakage risk of the ostomy appliance and/or indicative of the risk of skin damage to the user of the ostomy system.

In one or more exemplary accessory devices, determination of a moisture pattern type may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

The memory may be configured to store the monitor data and/or the leakage state.

The interface is configured to communicate the leakage state of the ostomy appliance to the user via the interface, such as an audio interface, a visual interface, and/or a transceiver module. An audio interface comprises for example a loudspeaker, and/or a microphone. A visual interface comprises for example a display. A transceiver module comprises for example an antenna and/or a radio transceiver.

In one or more accessory devices, the interface is configured to communicate the leakage state of the ostomy appliance by displaying, on a visual interface (e.g. a display) of the accessory device, a user interface comprising a user interface object representative of the leakage state, such as a first user interface object representative of a first leakage state, a second user interface object representative of a second leakage state, and/or a third user interface object representative of a third leakage state. The user interface object may be representative of one or more moisture pattern types determined, such as a first moisture pattern type, a second moisture pattern type, and/or a third moisture pattern type. In one or more accessory devices, the user interface object representative of the leakage state comprises one or more of a first user interface object, and a second user interface object, wherein the first and/or second user interface objects are indicative of one or more of a first leakage state in a primary sensing zone and/or a first zone, a second leakage state in a secondary sensing zone and/or a second zone and a third leakage state in a tertiary sensing zone and/or a third zone. For example, the user interface object may comprise one or more visual indicators representative of the leakage state, such as a first visual indicator for the first leakage state, a second visual indicator for the second leakage state, a third visual indicator for the third leakage state.

The processor may be configured to instruct the interface to display a user interface a first user interface object representative of a first leakage state based on the determination of the moisture pattern type. For example, when the moisture pattern type is determined, by the accessory device, to be indicative of a first moisture pattern type (as disclosed herein) and thereby the leakage state is determined by the accessory device to indicate to change NOW the ostomy appliance, the accessory device provides a user interface with a first user interface object reflecting the leakage state of the corresponding sensing zone or zone and the first moisture pattern type of the corresponding zone of the base plate by adapting the visual appearance of the first user interface object, e.g. in terms of colour, shade, and/or contrast.

The accessory device may comprise a user application configured to communicate the leakage state via the interface. The user application may be a dedicated ostomy application that assist the user in monitoring the internal leakage state of the ostomy appliance, and thereby reduce the likelihood of severe leakage reaching out to clothing of the user.

The present disclosure provides an ostomy appliance system comprising an ostomy appliance, an accessory device and a monitor device, the ostomy appliance comprising a base plate. The accessory device is configured to perform any of the methods disclosed herein.

The present disclosure provides a computer readable storage medium storing one or more programs, the one or more programs comprising instructions, which when executed by an accessory device with an interface, a memory and a processor cause the accessory device to perform any of the methods disclosed herein.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile device). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
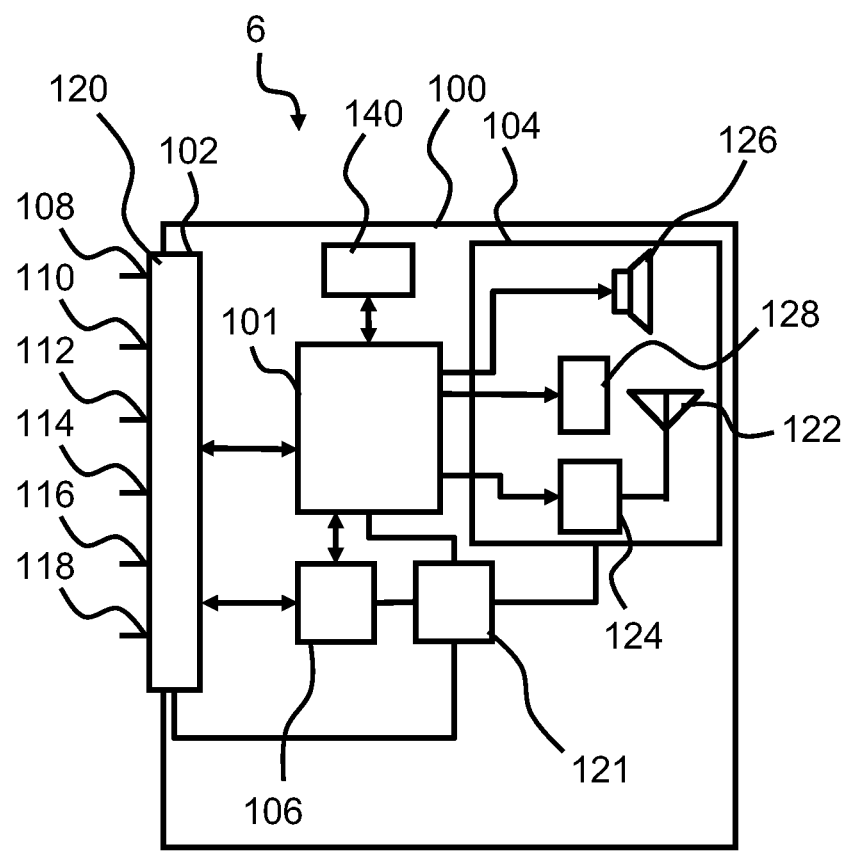
FIG. 2 illustrates an exemplary monitor device of the ostomy system.

FIG. 2 is a schematic block diagram of an exemplary monitor device. The monitor device 6 comprises a monitor device housing 100, 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
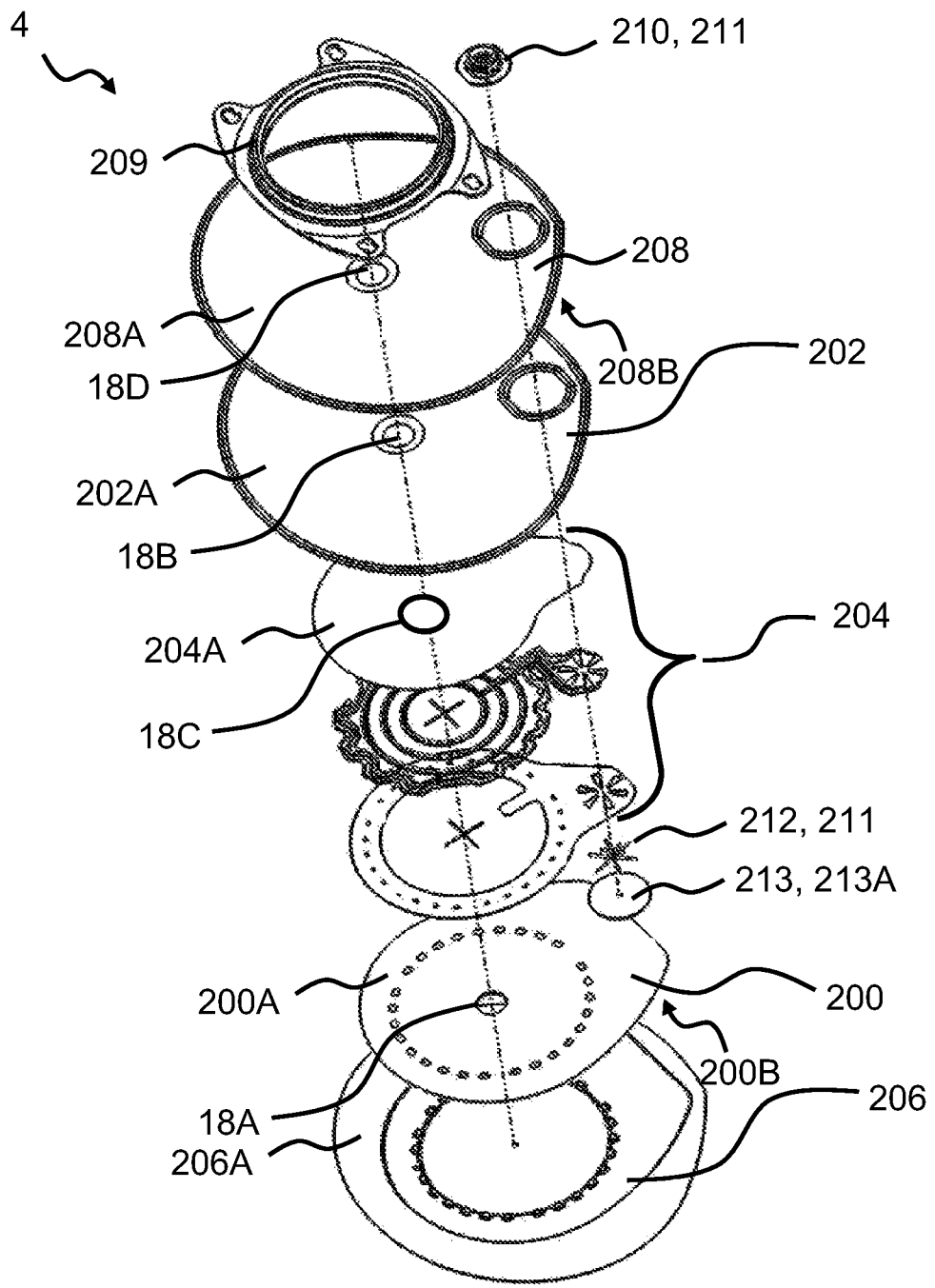
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204.

The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
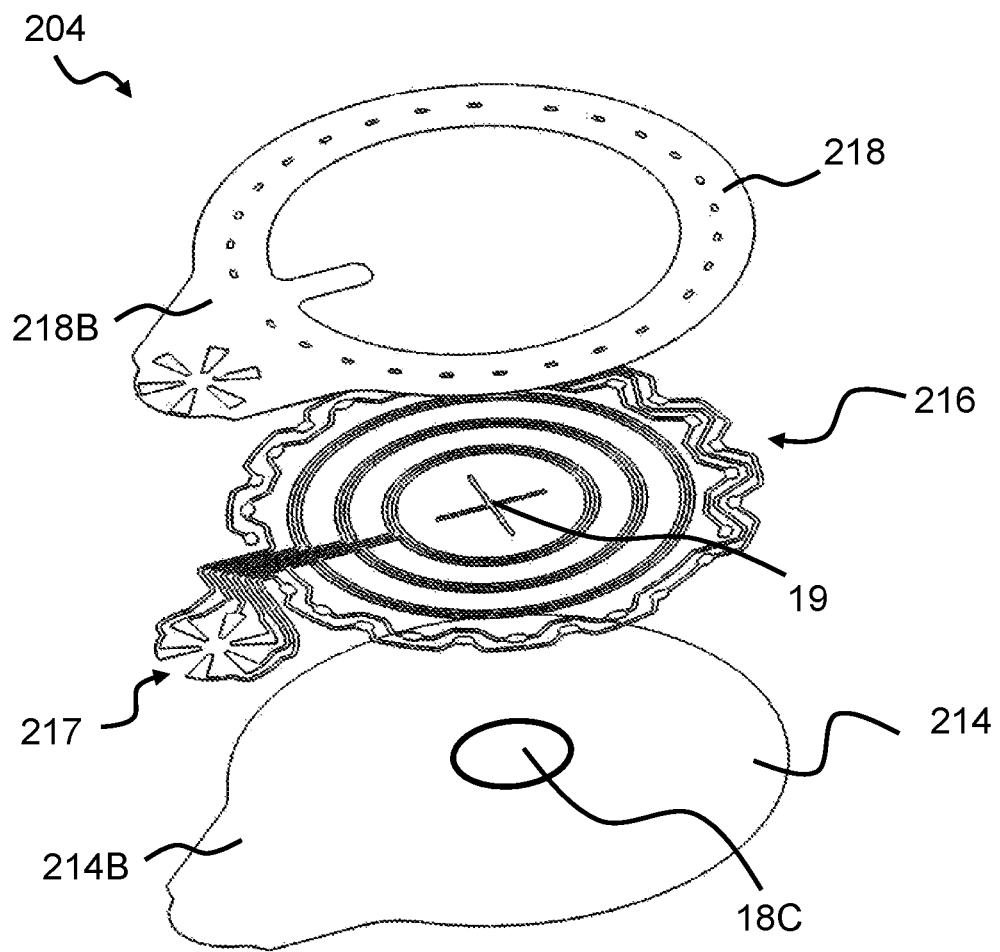
FIG. 4 is an exploded view of an exemplary electrode assembly.

FIG. 4 illustrates an exploded view of an exemplary electrode assembly 204 of a base plate. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
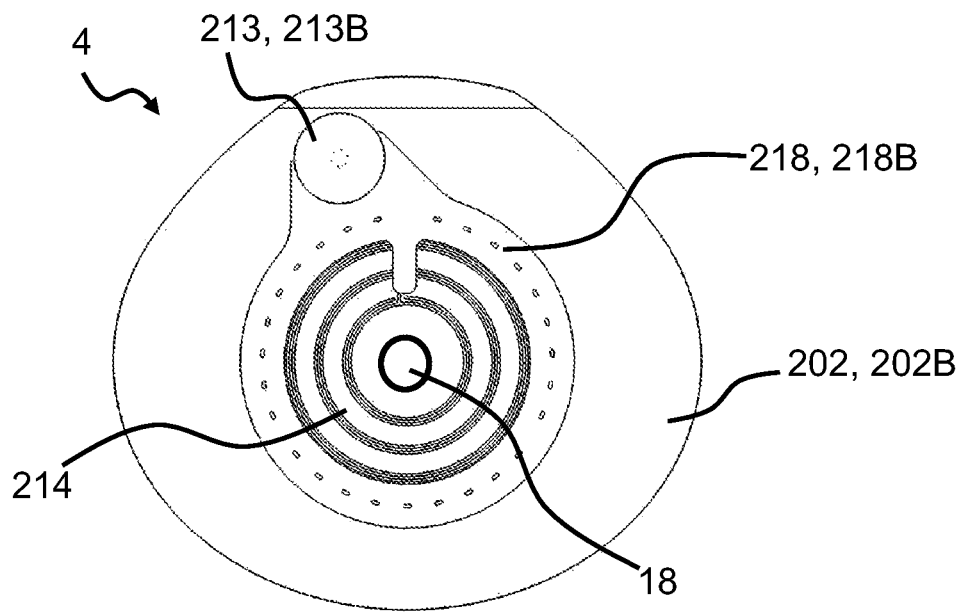
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
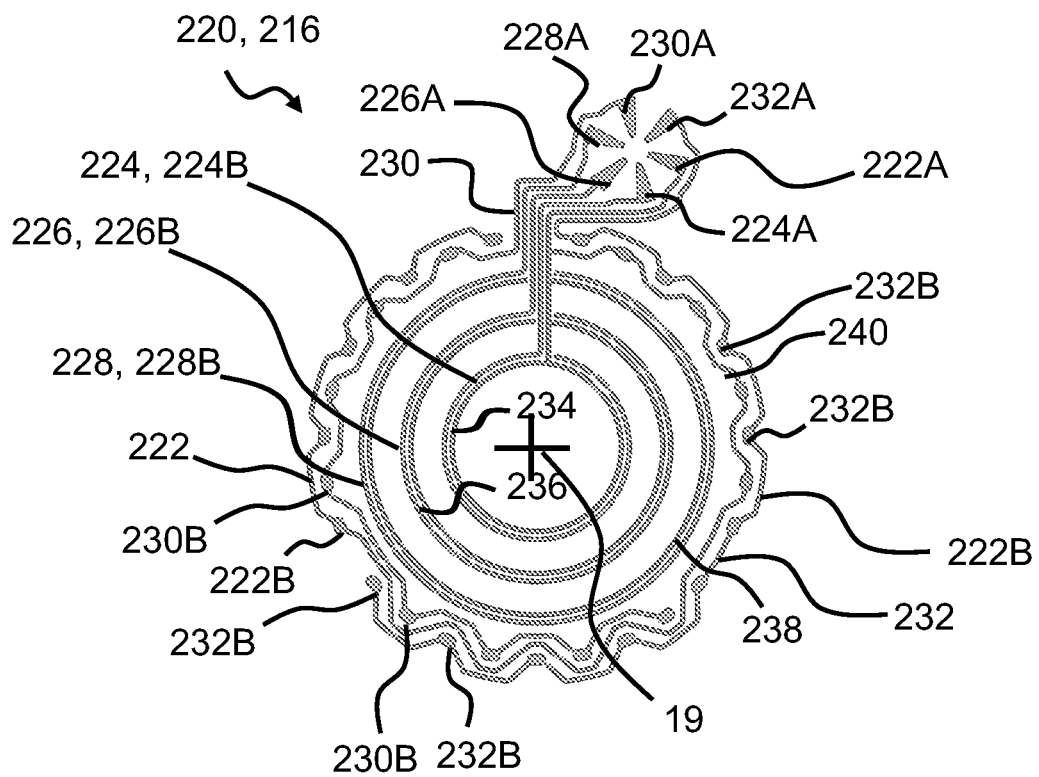
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
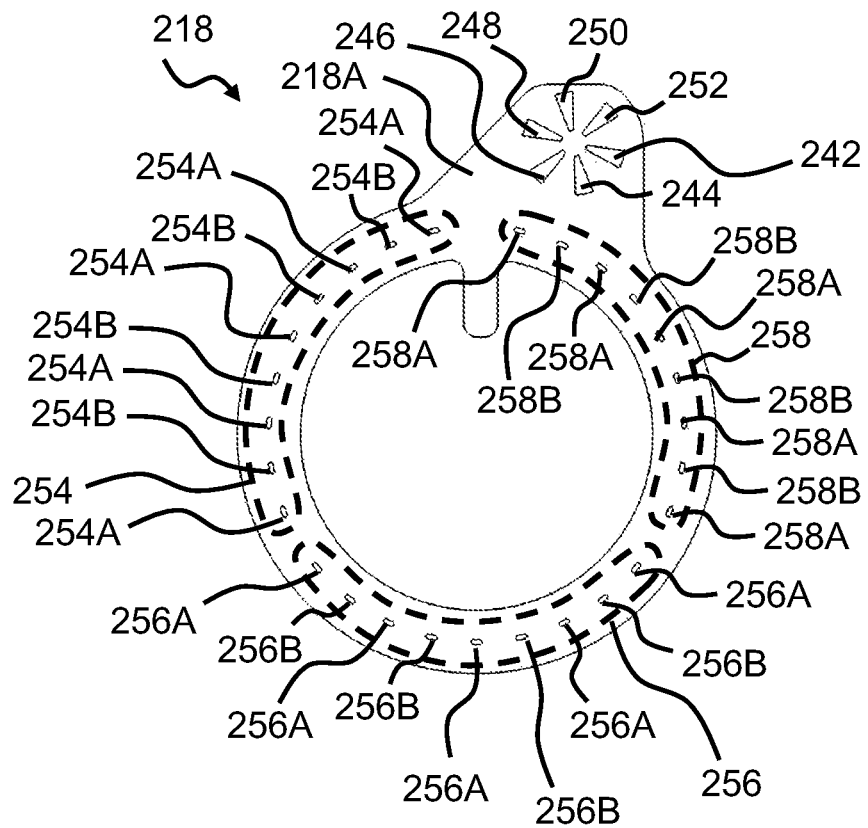
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
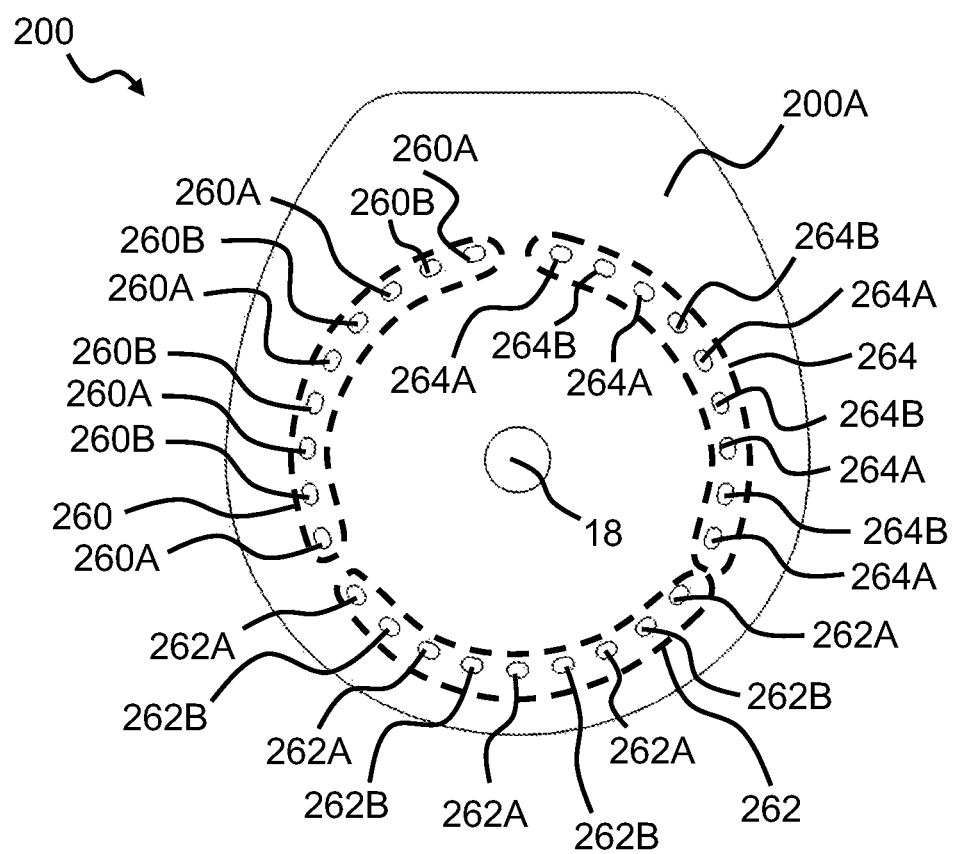
FIG. 8 is a distal view of an exemplary first adhesive layer.
Figure 9:
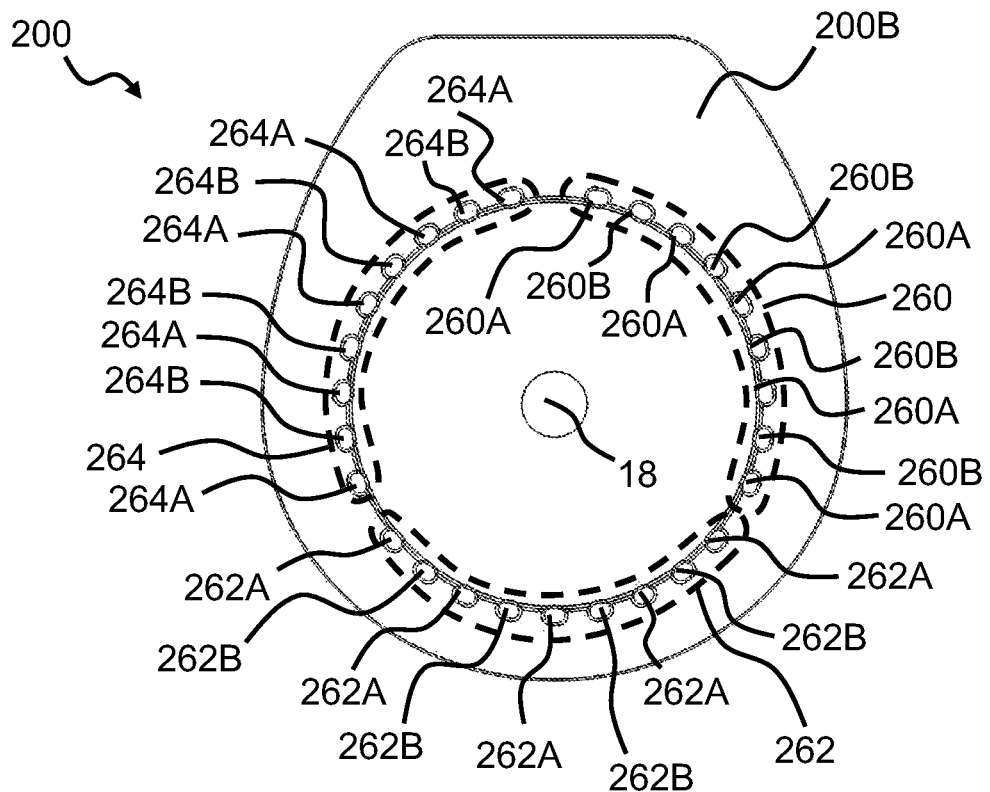
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
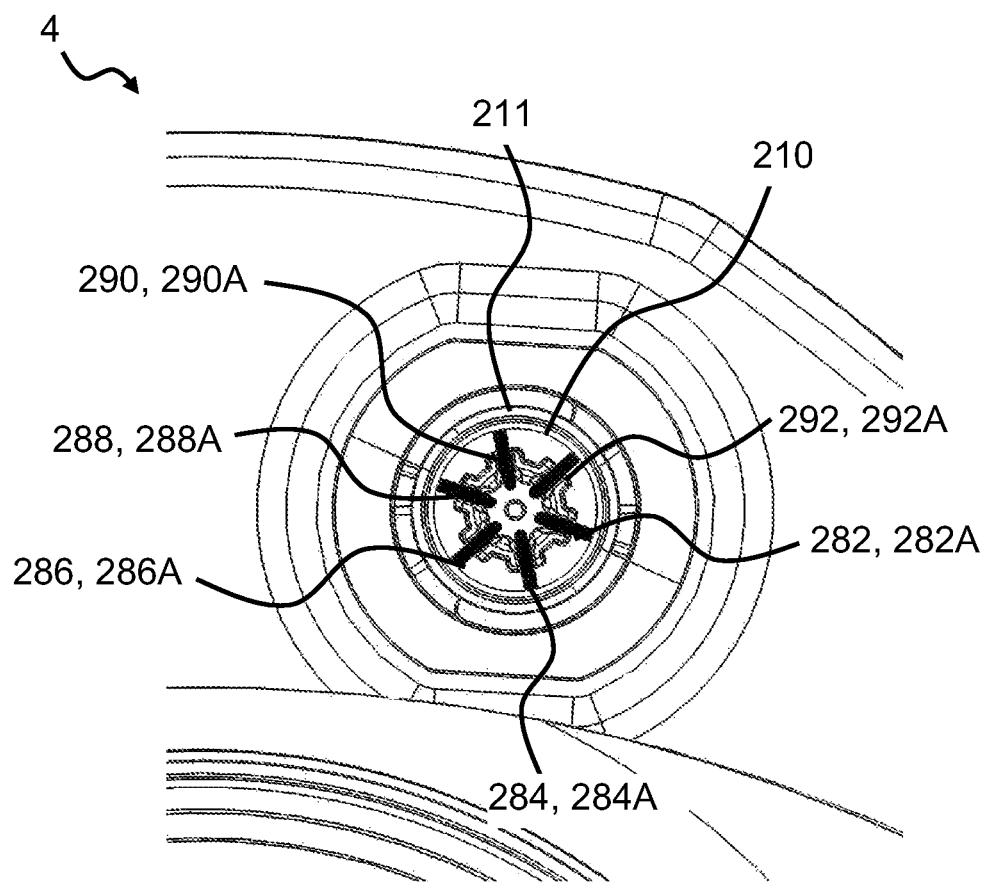
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 221/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
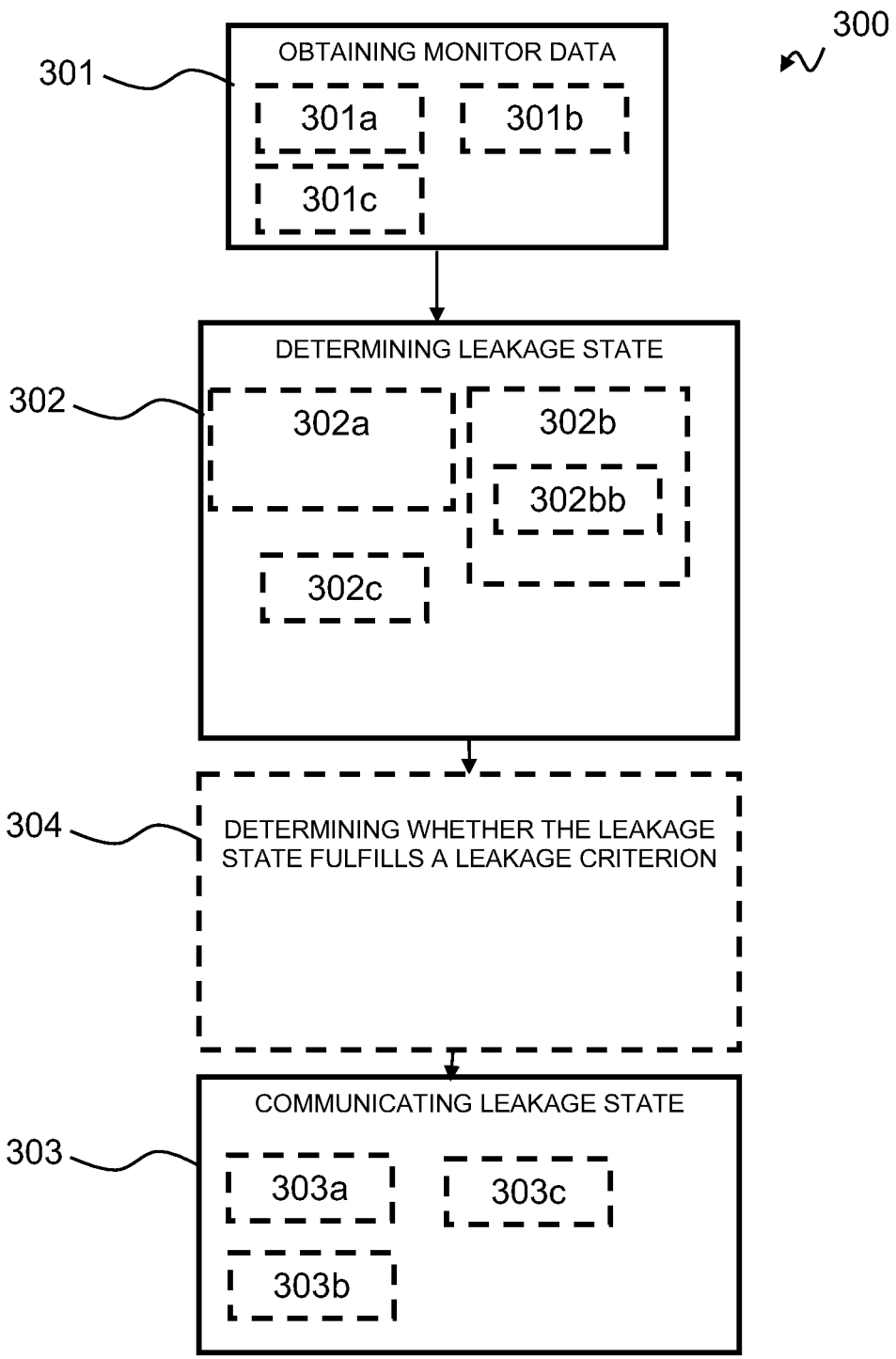
FIG. 11 illustrates an exemplary method of communicating the leakage state according to the present disclosure.

FIG. 11 illustrates an exemplary method 300 of communicating the leakage state according to the present disclosure. The method 300 is performed in an accessory device, for communicating the leakage state of the ostomy appliance, which in turn enables a monitoring leakage of the ostomy appliance at the accessory device. The accessory device comprises an interface configured to communicate with one or more devices of an ostomy system. The one or more devices comprise a monitor device, and/or an ostomy appliance configured to be placed on a skin surface of a user or on any additional seals.

The method 300 comprises obtaining 301 (e.g. receiving and/or retrieving) monitor data from the one or more devices. The monitor data is indicative of a presence of fluid of the ostomy appliance.

In one or more exemplary methods, the method 300 may comprise determining 302 a leakage state of the ostomy appliance based on the monitor data. A leakage state in the present disclosure is indicative of the dynamic internal state of the ostomy appliance, related to the presence of fluid (e.g. output, and/or feces) at the proximal side (or proximal surface) of the first adhesive layer of the ostomy appliance (between the skin surface and the proximal surface of the first adhesive layer) which is not visible to the user when the ostomy appliance is used. The leakage state may be indicative of adhesive performance of the ostomy appliance. The leakage state may be affected by several factors such as humidity, temperature, misplacement of the ostomy appliance on the stoma, and/or malfunction of the ostomy appliance and/or related to misplacement of the ostomy appliance on the stoma, and/or malfunction of the ostomy appliance. One or more factors alone or in combination impact the leakage state of the ostomy appliance. A leakage state in the present disclosure is configured to indicate whether the ostomy appliance needs to be changed based on its leakage state. For example, the leakage state may be indicative of the severity and/or imminence of the severe leakage, and thereby of the severity and/or imminence of the required change. The leakage state may comprise N leakage states, where N is an integer. For example, the leakage state may comprise a first leakage state for a first zone and/or a primary sensing zone. A first leakage state may comprise a first primary leakage state, a first secondary leakage state, a first tertiary leakage state (e.g. check, change in X time, change NOW, no leakage,).

The method comprises communicating 303 the leakage state of the ostomy appliance via the interface to the user or to the one or more devices. Communicating 303 may comprise outputting, transmitting and/or displaying the leakage state determined. In one or more exemplary methods, the method comprises determining 304 whether the leakage state fulfils a leakage criterion indicative of high risk (e.g. a severe leakage), and performing the step of communicating 303 the leakage state when the leakage state fulfils the leakage criterion. There may be several criteria, such as first criteria, second criteria, third criteria, a fourth criteria, a fifth criteria, and a sixth criteria.

In one or more exemplary methods, the ostomy appliance comprises an ostomy pouch and a base plate. In one or more exemplary methods, the base plate comprises a first adhesive layer having a proximal side (or proximal surface). In one or more exemplary methods, obtaining 301 the monitor data comprises obtaining 301a the monitor data indicative of the presence of fluid at the proximal side (or proximal surface) of the first adhesive layer of the base plate. The presence of fluid at the proximal side of the first adhesive layer creates a conductive path in the proximal surface of the first adhesive layer.

In one or more exemplary methods, the base plate comprises a plurality of electrodes configured to detect presence of fluid on the proximal side in a primary sensing zone (and/or a first zone) and a secondary sensing zone (and/or a second zone). The plurality of electrodes may include a first leakage electrode, a second leakage electrode, and a third leakage electrode. The first leakage electrode may serve as a ground electrode. The second leakage electrode may serve as the fourth electrode of the base plate embodiment disclosed herein. The third leakage electrode may serve as the fifth electrode of the base plate embodiment disclosed herein. The plurality of electrodes may include a first electrode, a second electrode, and a third electrode of the base plate embodiment disclosed herein. The In one or more exemplary methods, obtaining 301 monitor data comprises obtaining 301b data representative of detection of fluid on the proximal side (or proximal surface) in the primary sensing zone (and/or first zone) and the secondary sensing zone (and/or second zone).

In one or more exemplary methods, the monitor data comprises ostomy data and/or parameter data. For example, the parameter data is derived based on ostomy data. In one or more exemplary methods, obtaining 301 monitor data comprises obtaining ostomy data and/or parameter data. In one or more exemplary methods, obtaining 301 monitor data comprises obtaining the ostomy data and/or parameter data indicative of resistance between any two electrodes of the plurality of electrodes wherein at least one of the electrodes is a ground electrode, capacitance and/or inductance between electrodes between any two electrodes of the plurality of electrodes wherein at least one of the electrodes is a ground electrode and/or any change thereof. In one or more exemplary methods, the ostomy data and/or parameter data are indicative of a change in resistance, capacitance and/or inductance between any two electrodes of the plurality of electrodes wherein at least one of the electrodes is a ground electrode. In one or more exemplary methods, obtaining 301 monitor data comprises obtaining the ostomy data and/or parameter data comprising timing information, for e.g. a first primary sensing zone (and/or first zone), and optionally a second primary sensing zone (and/or second zone), such as timestamped data or information from which timing is derivable, for e.g. a first primary sensing zone (and/or first zone), and optionally a second primary sensing zone (and/or second zone).

In one or more exemplary methods, the monitor data comprises localized monitor data with respect to a location and/or zone on the base plate. The sensing zone and/or zone on the proximal side of the first adhesive layer of the base place may be related to a zone where the parameter data shows a drop or decrease in the resistance between two electrodes. In one or more exemplary methods, obtaining 301 the monitor data comprises obtaining 301c (e.g. receiving from one or more devices in the ostomy system, and/or retrieving from one or more devices in the ostomy system) localized monitor data with respect to a location and/or zone of the base plate, e.g. at the proximal side (e.g. proximal surface) of the first adhesive layer of the base plate. In one or more exemplary methods, the localized monitor data may be with respect to the primary sensing zone, the secondary sensing zone, and/or a tertiary sensing zone. In one or more exemplary methods, the monitor data may comprise first localized monitor data indicative of presence of fluid at the first zone, second localized monitor data indicative of presence of fluid at the second zone.

In one or more exemplary methods, determining 302 the leakage state of the ostomy appliance based on the monitor data comprises determining 302a the leakage location, and/or the leakage timing.

In one or more exemplary methods, determining 302 the leakage state of the ostomy appliance based on the monitor data comprises determining 302b one or more moisture pattern types based on the monitor data, such as based on the ostomy data and/or the parameter data (e.g. first parameter data and second parameter data by the leakage electrodes, such as indicating a drop or decrease in f resistance, capacitance and/or inductance satisfying a leakage criteria. The moisture pattern type is optionally indicative of adhesive failure of the base plate and/or leakage risk of the ostomy appliance and/or indicative of the risk of skin damage to the user of the ostomy system. In one or more exemplary methods, determining 302 the leakage state of the ostomy appliance based on the monitor data comprises determining one or more moisture pattern types based on the first parameter data and second parameter data (and optionally a third parameter) wherein the first parameter data is indicative of presence of fluid in the primary sensing zone (and/or first zone), and the second parameter data is indicative of presence of fluid in the secondary sensing zone (and/or second zone).

In one or more exemplary methods, determining 302b one or more moisture pattern types may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

In one or more exemplary methods determining 302b one or more moisture pattern types may comprise identifying 302bb the moisture pattern type based on the determination.

In one or more exemplary methods, determining 302 the leakage state of the ostomy appliance based on the monitor data comprises deriving 302c the leakage state based on the one or more moisture pattern types, such as a first moisture pattern type, a second moisture pattern type, and/or a third moisture pattern type, such as based on first parameter data indicative of presence of fluid in the primary sensing zone or in the first zone, second parameter data indicative of presence of fluid in the secondary sensing zone or in the second zone, and optionally third parameter data indicative of presence of fluid in the tertiary sensing zone or in the third zone.

In one or more exemplary methods, communicating 303 the leakage state of the ostomy appliance comprises displaying 303a, on a visual interface (e.g. a display) of the accessory device, a user interface comprising a user interface object representative of the leakage state, such as a first user interface object representative of a first leakage state in the primary sensing zone (and/or first zone), a second user interface object representative of a second leakage state in the secondary sensing zone (and/or second zone), and/or a third user interface object representative of a third leakage state in the tertiary sensing zone (and/or third zone). The first leakage state may comprise a first primary leakage state, a first secondary leakage state, a first tertiary leakage state (e.g. change NOW, check, change in X time, no leakage). The second leakage state may comprise a second primary leakage state, a second secondary leakage state, a second tertiary leakage state and/or a second quaternary leakage state (e.g. change NOW, check, change in X time, no leakage). The third leakage state may comprise a third primary leakage state, a third secondary leakage state, a third tertiary leakage state and/or a third quaternary leakage state (e.g. change NOW, check, change in X time, no leakage).

The user interface object may be representative of one or more moisture pattern types determined, such as a first moisture pattern type, a second moisture pattern type, and/or a third moisture pattern type. For example, the user interface object may comprise one or more visual indicators representative of the leakage state, such as a first visual indicator, a second visual indicator, a third visual indicator.

In one or more exemplary methods, communicating 303 the leakage state of the ostomy appliance comprises notifying 303b the user via the interface, such as by displaying a notification on a display of the accessory device. The notification may comprise the user interface object representative of the leakage state. The notification may comprise a notification indicator to open an application related to the ostomy appliance. The method may comprise detecting an input on the notification indicator, in response to the input, opening the application related to the ostomy appliance, and in response to the opening of the application, displaying the leakage state.

In one or more exemplary methods, the ostomy system comprises a server device. In one or more exemplary methods, communicating 303 the leakage state of the ostomy appliance comprises communicating 303c the leakage state of the ostomy appliance to the server device. For example, communication the leakage state of the ostomy appliance to the server device may comprise transmitting a message comprising the leakage state to the server device from the accessory device.

Figure 12:
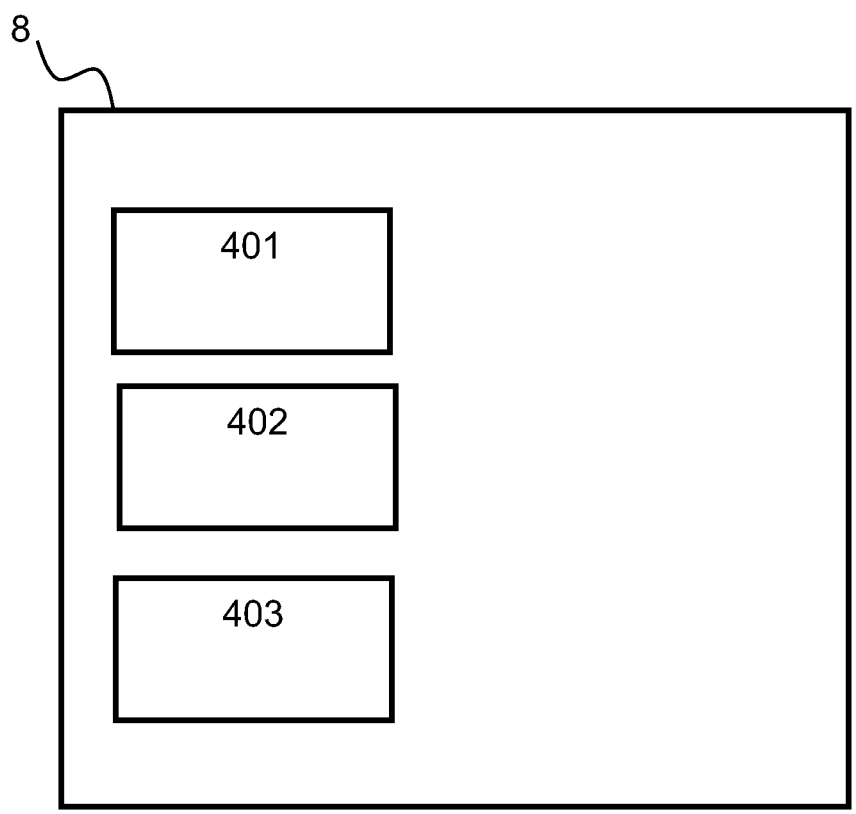
FIG. 12 illustrates an exemplary accessory device according to the present disclosure.

FIG. 12 is a block diagram illustrating an exemplary accessory device 8 according to the present disclosure. The accessory device 8 forms part of an ostomy system and is capable of supporting the monitoring and communication of the leakage state of an ostomy appliance to be placed on a user's skin. The accessory device 8 comprises a memory 401; a processor 402 coupled to the memory 401; and an interface 403 coupled to the processor 402.

Peripheral devices 401, 403 can be operatively and communicably coupled to the processor 402 via a bus for communicating data. The processor 402 can be a central processing unit (CPU), but other suitable microprocessors are also contemplated.

The interface 403 is configured to communicate with one or more devices of the ostomy system. The one or more devices comprising a monitor device, and/or an ostomy appliance configured to be placed on a skin surface of a user or on any additional seals. The interface 403 is configured to obtain monitor data from the one or more devices, such as to receive or retrieve the monitor data from the one or more devices. The monitor data may be indicative of a presence of fluid at a proximal side of the first adhesive layer of the ostomy appliance, such as a presence of fluid of a proximal side of the first adhesive layer of a base plate of the ostomy appliance.

The processor 402 may be configured to determine a leakage state of the ostomy appliance based on the monitor data obtained. The leakage state is indicative of the dynamic internal state of the ostomy appliance (for example early presence of fluid that is not visible to the user when the ostomy appliance is worn), related to the leakage of output (e.g. faecal material), such as severity, imminence, timing of leakage at a proximal side (or proximal surface) of the ostomy appliance. Presence of fluid on the proximal side (or proximal surface) of the first adhesive layer may affect the adhesive performance of the ostomy appliance. The processor 402 may be configured to determine the leakage state by determining a moisture pattern type. The moisture pattern type may be based on one or more, such as all, of first monitor data, second monitor data, and third monitor data, such as first parameter data, second parameter data and the third parameter data. The moisture pattern type may be based on the fourth parameter data.

The processor 402 is configured to determine one or more moisture pattern types based on the monitor data by identifying a moisture pattern type based on parameter data, such as for the corresponding zone, such first parameter data. Determining the leakage state of the ostomy appliance based on the monitor data comprises deriving the leakage state based on the one or more moisture pattern types, such as deriving a first leakage state for a primary sensing zone (and/or first zone) based on the first parameter data, deriving a second leakage state for a secondary sensing zone (and/or second zone) based on second parameter data, and/or deriving a third leakage state for a tertiary sensing zone (and/or third zone) based on third parameter data. In one or more exemplary methods, determining one or more moisture pattern types comprises determining whether at least one of the first parameter data, the second parameter data, and/or the third parameter data meets one or more of the first criteria, the second criteria, the third criteria, the fourth criteria, the fifth criteria, the sixth criteria respectively.

In one or more exemplary accessory devices, determination of a moisture pattern type may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

The memory 401 may be configured to store the monitor data and/or the leakage state. The processor 402 may be configured to instruct the interface 403 to display a user interface a first user interface object representative of a first leakage state based on the determination of the moisture pattern type. For example, when the moisture pattern type is determined, by the processor 402, to be indicative of a first moisture pattern type (as disclosed herein) and thereby the leakage state is determined by the processor 402 to indicate to change NOW the ostomy appliance, the accessory device provides instructions to the interface 403 to display a user interface with a first user interface object reflecting the leakage state of the corresponding sensing zone or zone and the first moisture pattern type of the corresponding zone of the base plate by adapting the visual appearance of the first user interface object, e.g. in terms of colour, shade, and/or contrast.

The interface 403 is configured to communicate the leakage state of the ostomy appliance to the user via the interface, such as an audio interface, a visual interface, and/or a transceiver module.

In one or more accessory devices, the interface 403 is configured to communicate the leakage state of the ostomy appliance by displaying, on a visual interface (e.g. a display) of the accessory device, a user interface comprising a user interface object representative of the leakage state, such as a first user interface object representative of a first leakage state, a second user interface object representative of a second leakage state, and/or a third user interface object representative of a third leakage state. The user interface object may be representative of one or more moisture pattern types determined, such as a first moisture pattern type, a second moisture pattern type, and/or a third moisture pattern type. In one or more accessory devices, the user interface object representative of the leakage state comprises one or more of a first user interface object, and a second user interface object, wherein the first and/or second user interface objects are indicative of one or more of a first leakage state, a second leakage state and a third leakage state. For example, the user interface object may comprise one or more visual indicators representative of the leakage state, such as a first visual indicator, a second visual indicator, a third visual indicator.

Figure 13A:
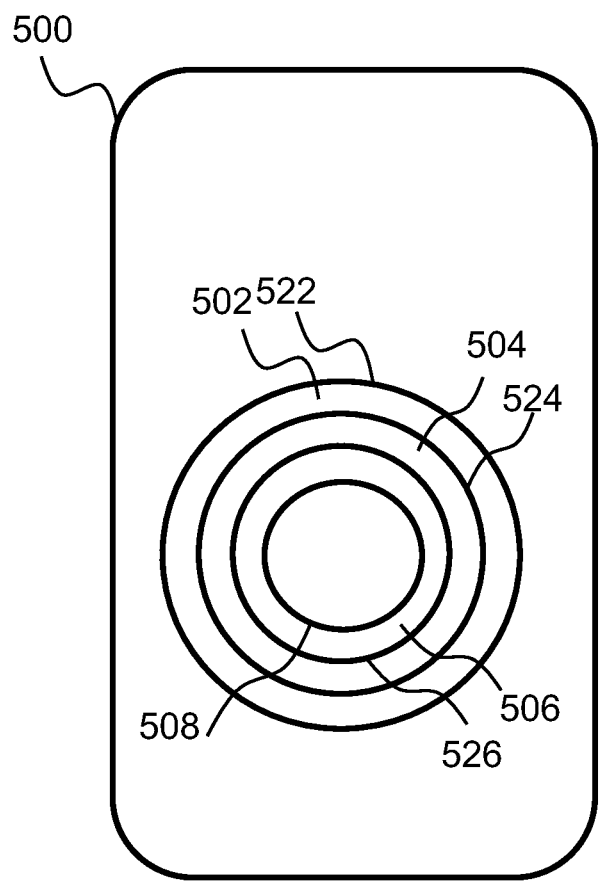
FIGS. 13a-c illustrate exemplary user interfaces for communicating the leakage state according to the present disclosure.
Figure 13B:
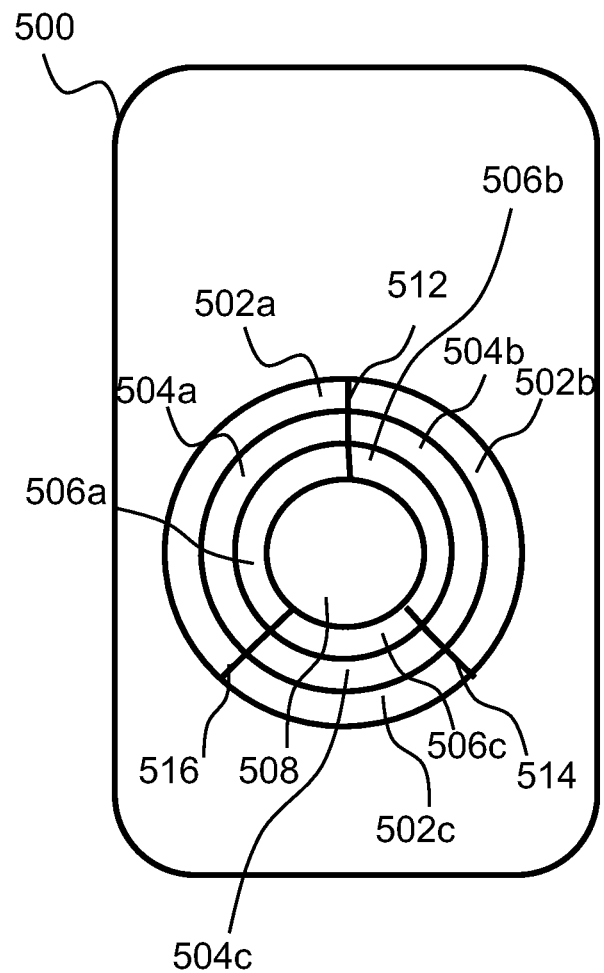
Figure 13C:
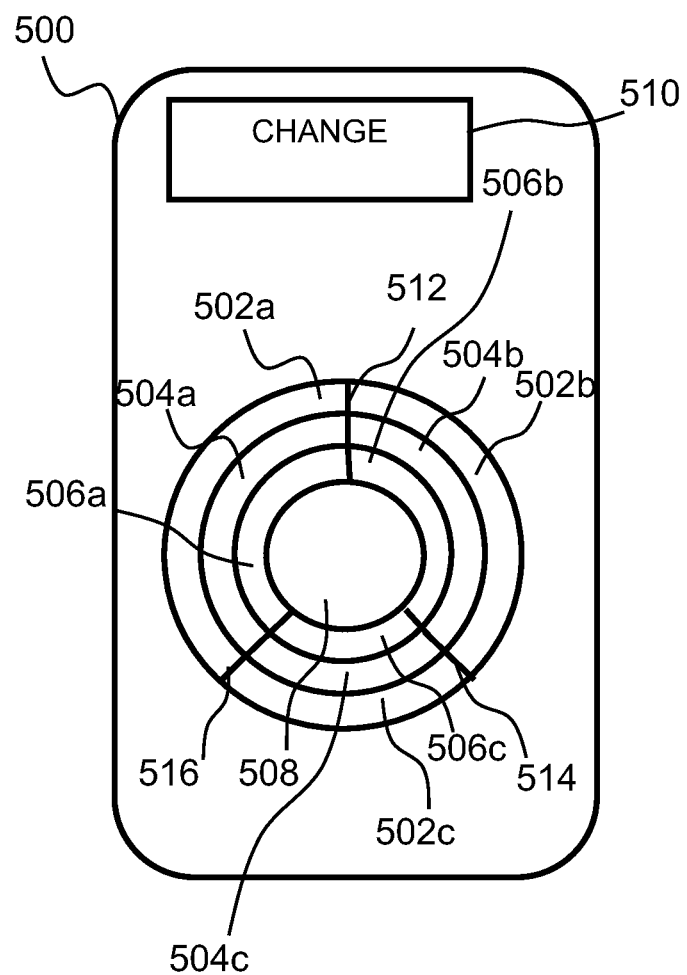

FIGS. 13a-c illustrate exemplary user interfaces for communicating the leakage state according to the present disclosure.

FIG. 13a shows an exemplary user interface 500 for communicating the leakage state of an ostomy appliance via an accessory device, such as via a visual interface of the accessory device. The user interface 500 comprises a plurality of visual indicators 502, 504, 506, 508, 522, 524, 526. Visual indicators 502, 504, 506 have the shape of a ring. Visual indicator 508, 522, 524, 526 has the shape of a circle. The user interface 500 comprises a central circle 508, a first circle 522, a first ring 502, a second circle 524, a second ring 504, a third circle 526, and a third ring 506. Each visual indicator 502, 504, 506, 508, 522, 524, 526 is arranged at a radial distance from the center of the first circle 508. The first ring 502, the second ring 504, and the third ring 506 are arranged concentrically around the first circle 508. It may be seen that the user interface is representative of a base plate of an ostomy appliance where the first circle 508 is representative of the stomal opening of the base plate and each of the first ring 502, the second ring 504, and the third ring 506 alone or in combination may define an area or a zone of the base plate.

The leakage state of the ostomy appliance is based on the moisture pattern type determined using parameter data obtained from one or more devices, such as a monitor device coupled with the base plate having electrodes placed in respective zones of the base plate (such as electrodes of FIG. 6 and/or sensor points openings of FIG. 7).

In one or more embodiments, the plurality of electrodes comprises a first electrode, a second electrode, and a third electrode, wherein the plurality of electrodes is configured to detect presence of fluid on the proximal side (or proximal surface) in a first zone, a second zone, a third zone of the base plate. The first zone is at a first radial distance from the center point of the stomal opening of the base plate. The second zone is at a second radial distance from the center point of the stomal opening of the base plate. The third zone is at a third radial distance from the center point of the stomal opening of the base plate. The first ring 502 may be representative of a first zone. The second ring 504 may be representative of a second zone. The third ring 506 may be representative of a third zone.

The visual appearance of any of the visual indicators 502, 504, 506, 508 may be configured to change dynamically based on the leakage state (e.g. degree of leakage state) of the ostomy appliance (i.e. so that the visual indicator reflects the current leakage state of the ostomy appliance as determined by the accessory device based on the monitor data obtained). The visual appearance of any of the visual indicators 502, 504, 506, 508 may be configured to change dynamically in terms of colour, shape, form, contrast, brightness, animation and/or blurring to indicate the leakage state. For example, the severity of the leakage state may be displayed by varying in colour: e.g. blue, yellow, red for indicating low, medium, high severity (e.g. no leakage, or very low, low, high risk) respectively. For example, the severity of the leakage state may be displayed by varying shades within a colour from a lighter shade to a darker shade for indicating low to high severity (e.g. low to high risk) respectively. For example, the severity of the leakage state may be displayed by varying a magnitude of the visual effect (e.g., more blurring) as severity increases. For example, a (first, second, or third) primary leakage state may be represented by a first visual appearance of the corresponding visual indicator, e.g. of the corresponding ring. For example, a (first, second, or third) secondary leakage state may be represented by a second visual appearance of the corresponding visual indicator, e.g. of the corresponding ring. For example, a (first, second, or third) tertiary leakage state may be represented by a third visual appearance of the corresponding visual indicator, e.g. of the corresponding ring. For example, a (first, second, or third) quaternary leakage state may be represented by a fourth visual appearance of the corresponding visual indicator, e.g. of the corresponding ring. For example, a (first, second, or third) primary leakage state is indicative of high risk (e.g. high severity and/or high imminence) of leakage e.g.: change NOW. For example, a (first, second, or third) secondary leakage state is indicative of low risk (e.g. low severity and/or low imminence) of leakage e.g.: check or change in X time. For example, a (first, second, or third) tertiary leakage state is indicative of very low risk (e.g. very low severity and/or very low imminence of severe leakage) of leakage e.g.: check or change in X time. For example, a (first, second, or third) quaternary leakage state is indicative of no leakage (i.e. no presence of fluid on the proximal surface of the first adhesive layer). It may be envisaged that the visual appearance is selected based on risk level of the leakage state.

The accessory device is configured to change dynamically the visual appearance of any of the rings in terms of e.g. colour, shape, form, contrast, brightness, animation and/or blurring in accordance with the leakage state (so as to reflect the determined moisture pattern type). For example, when the moisture pattern type is determined, by the accessory device, to be indicative of high severity (e.g. first moisture pattern type) and thereby the leakage state indicates to change NOW the ostomy appliance, the accessory device provides a user interface 500 with first ring 502 reflecting the leakage state derived from the monitor data indicating presence of fluid in the first zone and indicating the first moisture pattern type of the corresponding first zone of the base plate by adopting e.g. the colour red, in a dark shade, in sharp contrast.

Additionally, or alternatively, when any of the leakage state is indicative of an acute leakage, corresponding to change NOW, any of the visual indicators 502, 504, 506, 508 may be configured to be displayed with a single visual appearance (such as a single colour, such as red) to indicate clearly and unambiguously that the leakage state is of high risk and needs immediate attention.

As illustrated in FIG. 13b, in one or more exemplary user interfaces, the user interface 500 comprises a plurality of angular visual delimiters (such as a first angular visual delimiter 512, a second angular visual delimiter 514, a third angular visual delimiter 516). The user interface 500 comprises a first primary ring part 502a, a first secondary ring part 502b, a first tertiary ring part 502c, a second primary ring part 506a, a second secondary ring part 506b, a second tertiary ring part 506c, a third primary ring part 506a, a third secondary ring part 506b, and/or a third tertiary ring part 506c.

It may be seen that the base plate comprises a plurality of electrodes, e.g. leakage electrodes, configured to detect presence of fluid on the proximal side (or proximal surface) in one or more primary sensing zones (represented by a first primary ring part 502a, a second primary ring part 504a, a third primary ring part 506a), one or more secondary sensing zones (such as a first secondary ring part 502b, a second secondary ring part 504b, a third secondary ring part 506b), one or more tertiary sensing zones (such as a first tertiary ring part 502c, a second tertiary ring part 504c, a third tertiary ring part 506c). In one or more embodiments, the plurality of electrodes may include a first leakage electrode, a second leakage electrode, and a third leakage electrode, wherein any two of the leakage electrodes are configured to detect presence of fluid on the proximal side in a primary sensing zone and a secondary sensing zone. The first leakage electrode may comprise one or more primary first sensing parts arranged in the primary sensing zone. The second leakage electrode may comprise one or more primary second sensing parts arranged in the primary sensing zone. The second leakage electrode may comprise one or more secondary second sensing parts arranged in the secondary sensing zone (e.g. sensor point openings of FIG. 7). The third leakage electrode may comprise one or more secondary third sensing parts arranged in the secondary sensing zone (e.g. sensor point openings of FIG. 7). The primary sensing zone may be arranged in a primary angle space from the center point of the first adhesive layer and the secondary sensing zone may be arranged in a secondary angle space from the center point of the first adhesive layer. The primary angle space may span a primary angle in the range from 45° to 315°. The secondary angle space may span a secondary angle in the range from 45° to 315°. The primary sensing zone and the secondary sensing zone may be separate sensing zones, such as non-overlapping sensing zones. The sensing parts may be place at equal distance from the center point.

It may be seen that the ring parts 502a, 504a, and 506a form a primary ring part that is arranged in a primary angle space from the center point of the first circle 508. It may be seen that the ring parts 502b, 504b, and 506b form a secondary ring part that is arranged in a secondary angle space from the center point of the first circle 508). It may be seen that the ring parts 502c, 504c, and 506c form a tertiary ring part that is arranged in a tertiary angle space from the center point of the first circle 508. The primary angle space may be arranged to span a primary angle in the range from 45° to 315°. The secondary angle space may be arranged to span a secondary angle in the range from 45° to 315°. The tertiary angle space may be arranged to span a tertiary angle in the range from 45° to 315°.

The accessory device of may be configured to change dynamically the visual appearance of any of the ring parts, e.g. in terms of colour, shape, form, contrast, brightness, animation and/or blurring in accordance with the leakage state, e.g. in accordance with determination of the moisture pattern type. The accessory device is configured to change dynamically the visual appearance of any of the ring parts in terms of e.g. colour, shape, form, contrast, brightness, animation and/or blurring in accordance with the leakage state (so as to reflect the determined moisture pattern type). For example, when the moisture pattern type is determined, by the accessory device, to be indicative of high severity (e.g. first moisture pattern type) and thereby the leakage state indicates to change NOW the ostomy appliance, the accessory device provides a user interface 500 with first primary ring part 502a reflecting the leakage state of the corresponding primary sensing zone and the first moisture pattern type of the corresponding primary sensing zone of the base plate by adopting e.g. the colour red, in a dark shade, in sharp contrast.

It may be seen that the first primary ring part 502a, first secondary ring part 502b, the first tertiary ring part 502c are indicative of the leakage state of the first zone or the primary sensing zone, any of which is represented by a first ring 502. The same applies to ring parts 504a, 504b, 504c forming part of second ring 504, and to ring parts 506a, 506b, 506c forming parts of third ring 506.

The monitor data may be seen as indicative of the leakage state of the ostomy appliance. The visual appearance of the visual indicators is indicative of the leakage state of the ostomy appliance, such as indicative of the moisture pattern type determined by the accessory device.

As illustrated in FIG. 13c, in one or more exemplary user interfaces, the user interface 500 comprises a visual indicator which is a text prompt 510 indicating to the user the dynamic internal leakage state of the ostomy appliance. A text prompt 510 may for example indicate: "Everything is fine", "Good", "Check", "Change", "Change NOW".

The accessory device may be configured to provide the user interface 500 of FIG. 13a-c in a user application running on the processor. The accessory device may comprise a user application configured to communicate the leakage state via the interface. The user application may be a dedicated ostomy application that assist the user in monitoring the internal leakage state of the ostomy appliance, and thereby reduce the likelihood of severe leakage reaching out to clothing of the user.

Figure 14:
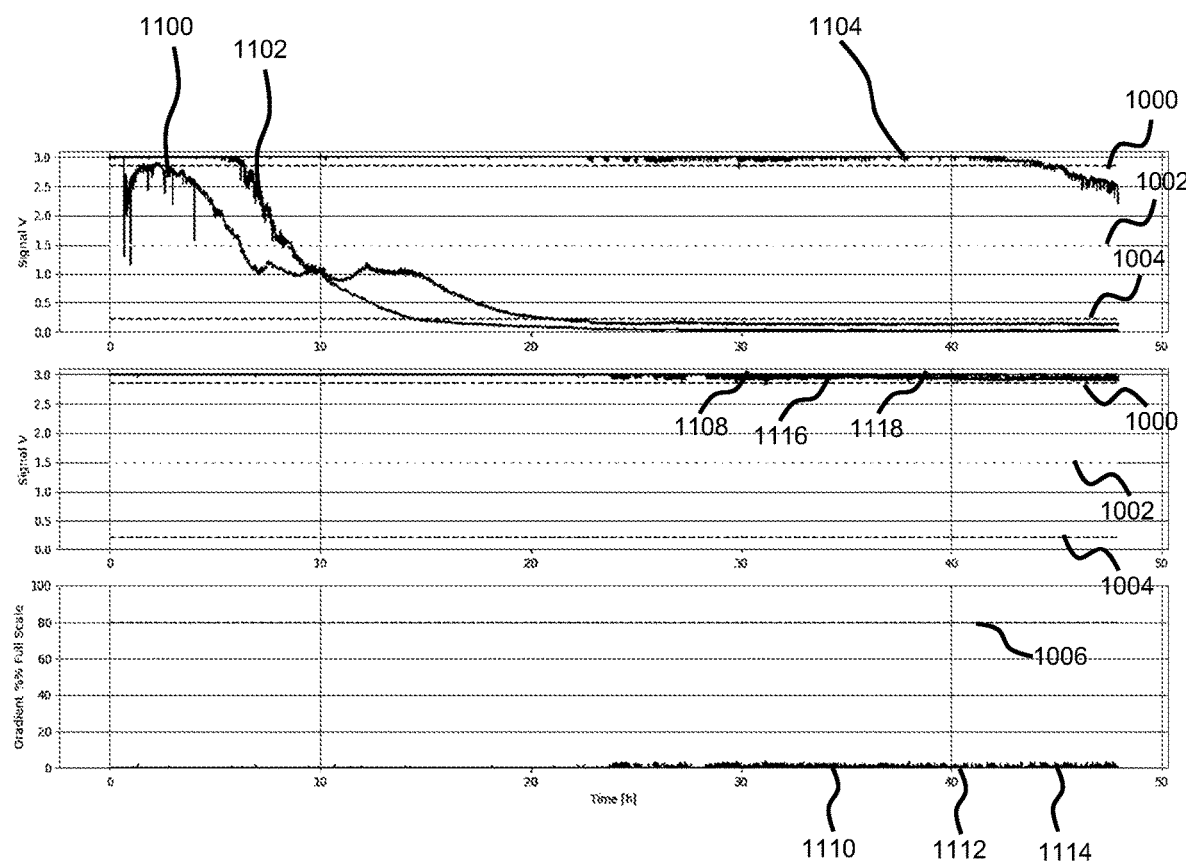
FIG. 14 is an exemplary graphical representation of parameter data as a function of time.

FIG. 14 shows an exemplary graphical representation of parameter data as a function of time. In this example, the parameter data in the y-axis is in Volts and time is in the x-axis. Curve 1100 shows, as a function of time, first parameter data indicative of voltage measured by the first electrode pair of the base plate. Curve 1102 shows, as a function of time, a second parameter data indicative of voltage measured by the second electrode pair of the base plate. Curve 1104 shows, as a function of time, third parameter data indicative of voltage measured by the third electrode pair of the base plate. Curves 1108, 1116, 1118 show, as a function of time, a fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1110, 1 112, 1114 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 14 shows the upper voltage threshold value represented as curve 1000, the medium voltage threshold value represented as curve 1002, the lower voltage threshold value represented as curve 1004, and curve 1006 is a gradient limit.

Curves 1108, 1116, 1118 as well as curves 1110, 1112, 1114 show that no moisture is detected at the proximal side of the first adhesive layer by the fourth electrode pair.

At a time less than 5 h, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the ostomy appliance is in a first operating state.

At time between 5 h and 10 h, curve 1102 shows that moisture is detected by the second electrode pair as the second parameter data crosses the upper voltage threshold value. At this stage, it is determined that the ostomy appliance is in a second operating state.

At time around 45 h, curve 1104 shows that moisture is detected by the third electrode pair as the third parameter data crosses the upper voltage threshold value. At this stage, it is determined that the ostomy appliance is in a third operating state.

Figure 15:
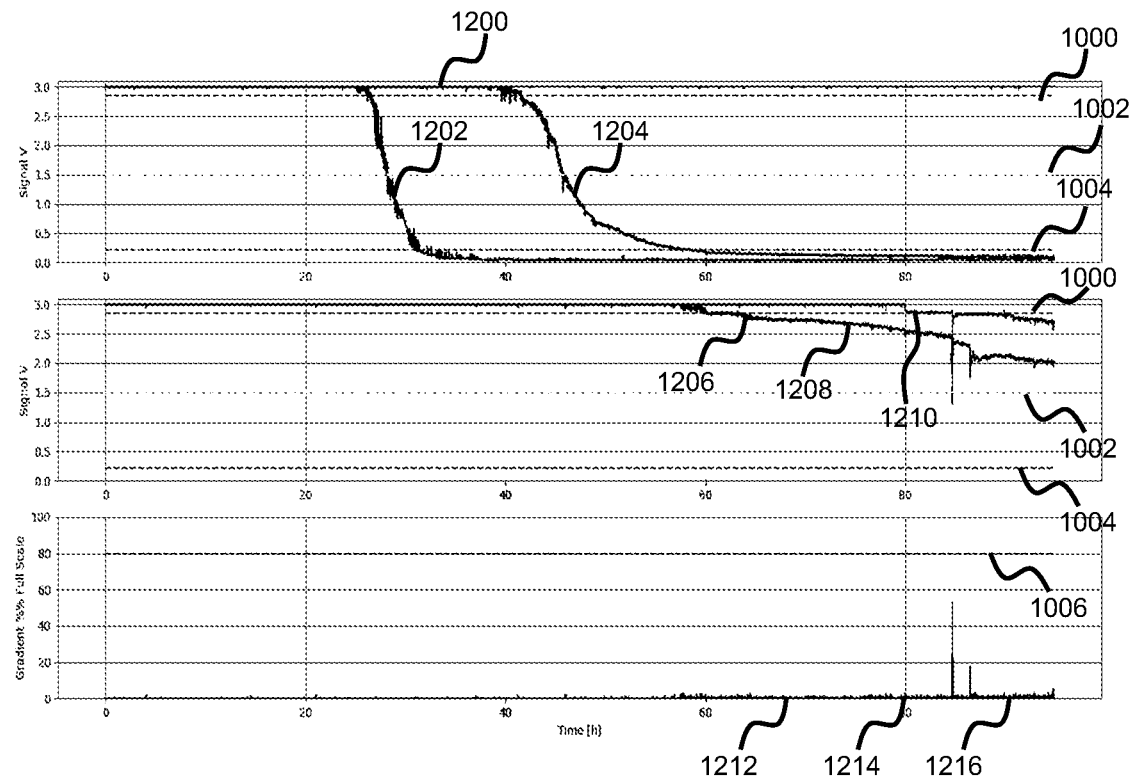
FIG. 15 is an exemplary graphical representation of parameter data as a function of time.

FIG. 15 shows an exemplary graphical representation of parameter data as a function of time. In this example, the parameter data in the y-axis is in Volts and time is in the x-axis. Curve 1202 shows, as a function of time, first parameter data indicative of voltage measured by the first electrode pair of the base plate. Curve 1204 shows, as a function of time, second parameter data indicative of voltage measured by the second electrode pair of the base plate. Curve 1200 shows, as a function of time, third parameter data indicative of voltage measured by the third electrode pair of the base plate. Curves 1206, 1208, 1210 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1212, 1214, 1216 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 15 shows the upper voltage threshold value represented as curve 1000, the medium voltage threshold value represented as curve 1002, the lower voltage threshold value represented as curve 1004, and curve 1006 represents a gradient limit.

Curves 1206, 1208, 1210 as well as curves 1212, 1214, 1216 show that moisture is detected at the proximal side of the first adhesive layer by the fourth electrode pair, the fourth and fifth electrode, and the fifth electrode pair at a time starting at 60 h until 90 h. As the three electrode pairs are triggered as shown by the decreases shown by 1206, 1208, 1210 and as the curves 1212, 1214, 1216 show a gradient below 80%, this is indicative of the presence of sweat at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the ostomy appliance is in a first operating state.

At time around 40 h, curve 1204 shows that moisture is detected by the second electrode pair as the second parameter data crosses the upper voltage threshold value. At this stage, it is determined that the ostomy appliance is in a second operating state.

Figure 16:
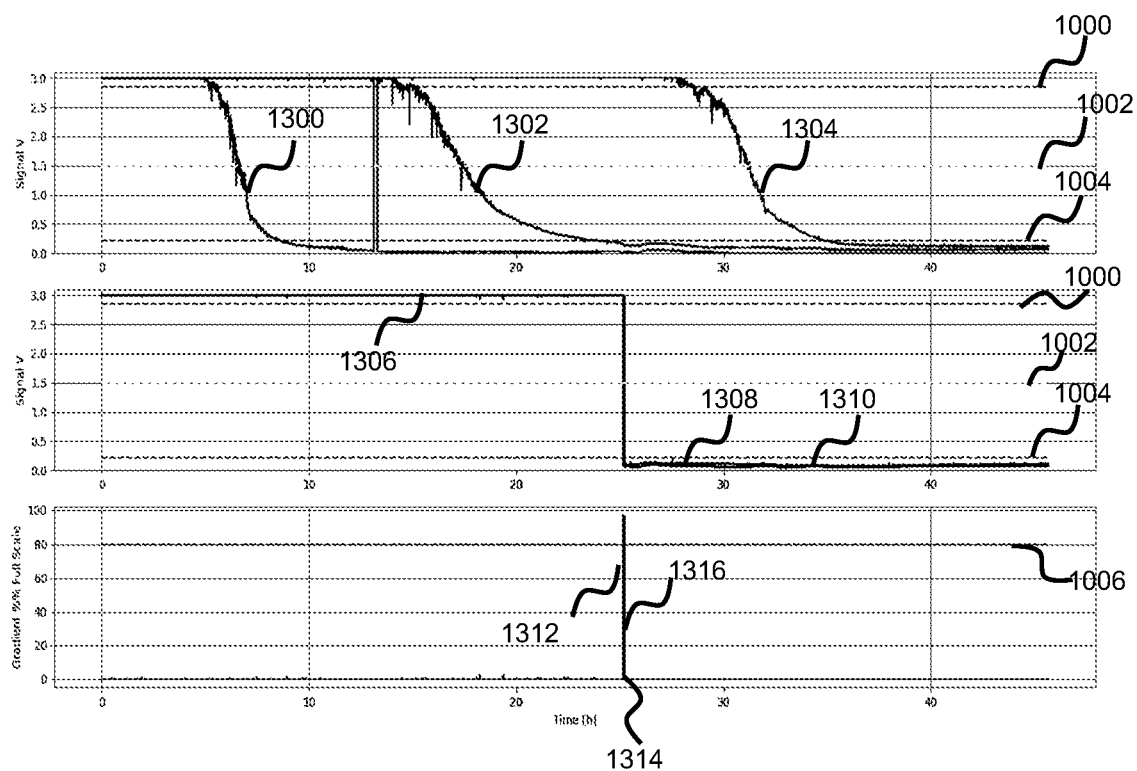
FIG. 16 is an exemplary graphical representation of parameter data as a function of time.

FIG. 16 shows an exemplary graphical representation of parameter data as a function of time. In this example, the parameter data in the y-axis is in Volts and time is in the x-axis. Curve 1300 shows, as a function of time, first parameter data indicative of voltage measured by the first electrode pair of the base plate. Curve 1302 shows, as a function of time, a second parameter data indicative of voltage measured by the second electrode pair of the base plate. Curve 1304 shows, as a function of time, third parameter data indicative of voltage measured by the third electrode pair of the base plate. Curves 1306, 1308, 1310 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1312, 1314, 1316 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively FIG. 16 shows the upper voltage threshold value represented as curve 1000, the medium voltage threshold value represented as curve 1002, the lower voltage threshold value represented as curve 1004, and curve 1006 is a gradient limit.

Curves 1306, 1308, 1310 as well as curves 1312, 1314, 1316 show that moisture is detected at the proximal side of the first adhesive layer by the fourth electrode pair at a time starting at around 25 h. As the three parts of the fourth electrode pair are trigger as shown by the decreases shown by 1306, 1308, 1310 and as the curves 1312, 1314, 1316 show a gradient above 80%, this is indicative of the presence of output at the proximal side of the first adhesive layer. This indicate severe leakage.

At a time of 5 h, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the ostomy appliance is in a first operating state.

At time around 15 h, curve 1302 shows that moisture is detected by the second electrode pair as the second parameter data crosses the upper voltage threshold value. At this stage, it is determined that the ostomy appliance is in a second operating state.

At time around 30 h, curve 1304 shows that moisture is detected by the third electrode pair as the third parameter data crosses the upper voltage threshold value. In an example where the curves 1306, 1308, 1310 had not dropped below corresponding thresholds, curve 1304 indicates that moisture has reached the third electrode pair, and the present disclosure enables determining that the ostomy appliance is in a third operating state.

Figure 17:
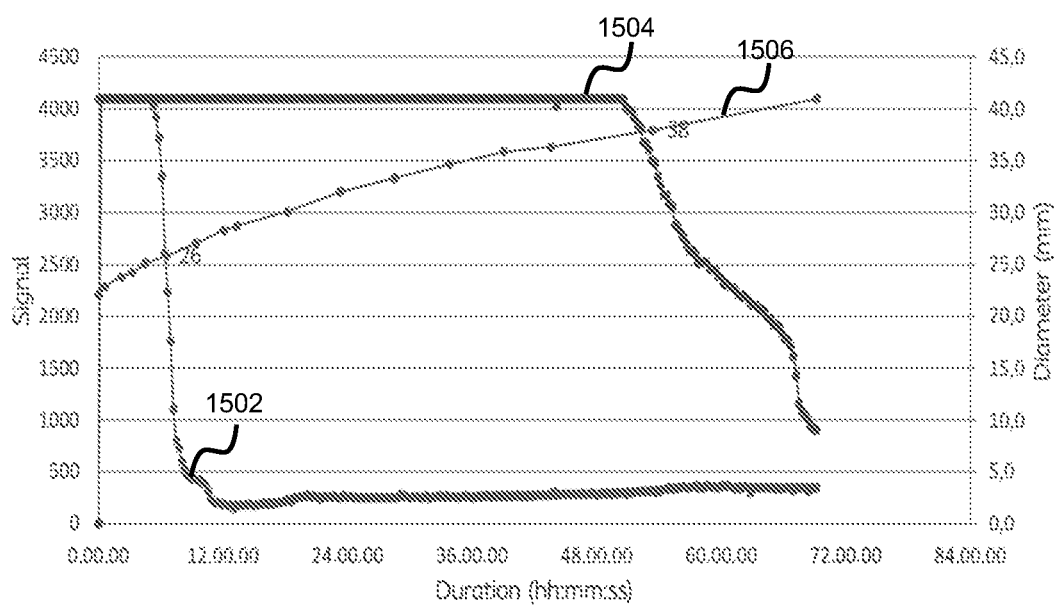
FIG. 17 is an exemplary graphical representation of parameter data as a function of time and a whitening zone diameter as a function of time.

FIG. 17 shows an exemplary graphical representation of parameter data as a function of time and a whitening zone diameter (e.g. related to a radial thickness of a whitening ring surrounding the stomal opening) as a function of time. FIG. 17 illustrates the moisture propagation in the first adhesive layer as a function of time, and illustrates a correlation between parameter data detected by the first electrode pair and the second electrode pair of the base plate and actual moisture on the proximal surface of the first adhesive layer of the base plate. The actual moisture propagation in the first adhesive layer may appear as a whitening zone (e.g. a white ring around the stomal opening) in the first adhesive layer. Moisture affects the first adhesive layer in that the moisture reacts with the composition of the first adhesive layer to form the white ring around the stomal opening, and thereby reduces adhesive performance of the base plate. FIG. 17 is obtained by experiments where water is applied from the stomal opening of the based plate to follow, using the electrodes of the base plate, the radial propagation of moisture leading to radial erosion of the first adhesive layer of the base plate.

Curve 1502 shows, as a function of time, first parameter data indicative of voltage measured by the first electrode pair of the base plate. Curve 1504 shows, as a function of time, a second parameter data indicative of voltage measured by the second electrode pair of the base plate. Curve 1506 shows a diameter of the white ring as a function of time. The first parameter data shows a decrease in e.g. voltage measured by the first electrode pair over time. It is also seen that the voltage of the second electrode pair drops at a later time than when the first parameter data shows a decrease in e.g. voltage dropped. This correlates well with the diameter of the white ring which goes from around 25-26 mm when the first electrode pair is triggered (e.g. first parameter data shows a decrease) to 38 mm when the second electrode pair is triggered (second parameter data shows a decrease). This corresponds substantially to the location of the first electrode pair at twice the first radial distance R1, and of the second electrode pair at twice the second radial distance R2.

It is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 mm (recommended by a nurse), between 10 mm and 20 (for a user in compliance with a preferred use), and/or between 20 mm and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclose methods, ostomy appliances, monitor devices, and accessory devices allow to accommodate the regional preferences of user in their use of the ostomy appliance so as to adjust thresholds for the operating states to the regional preference or use.

Figure 18A:
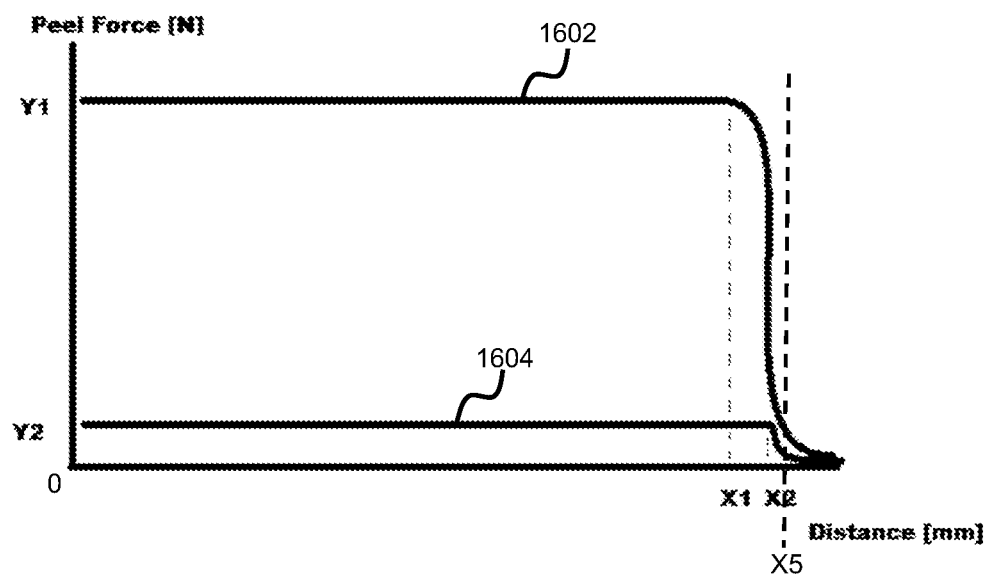
FIGS. 18A-18B are exemplary graphical representations of peel force as a function of a peeling distance travelled by a peeling action exercising the peel force on a first adhesive layer of a base plate.
Figure 18B:
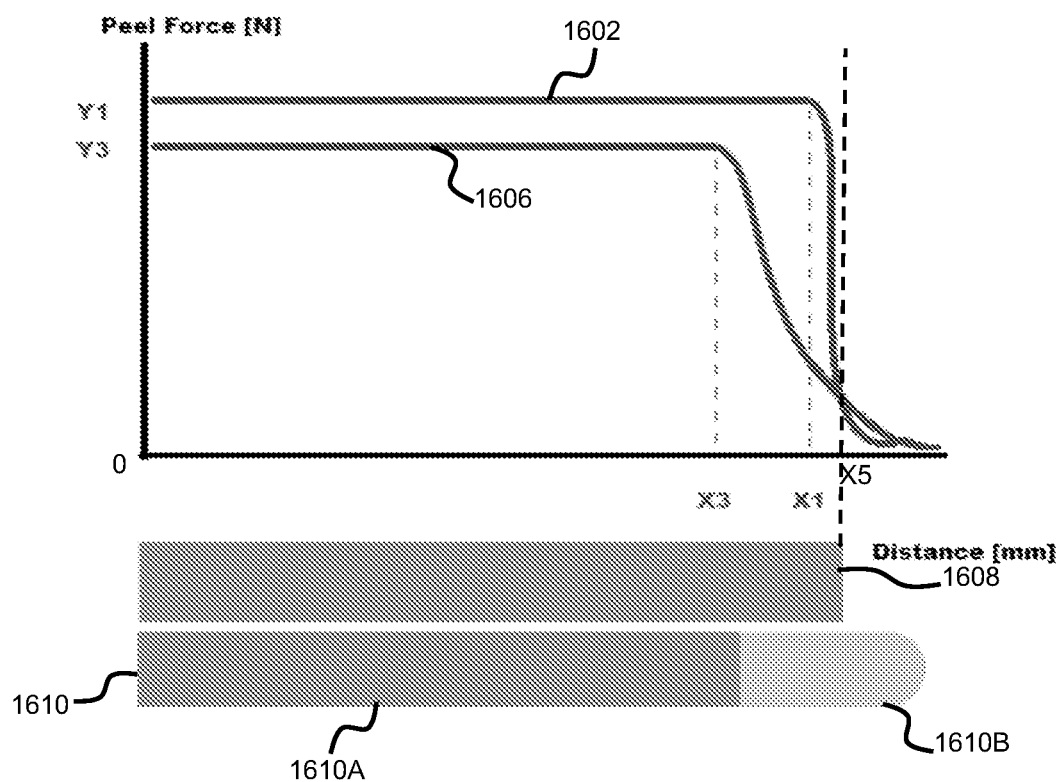

FIGS. 18A-18B shows exemplary graphical representations of peel force as a function of a peeling distance travelled by a peeling action exercising the peel force on a first adhesive layer of a base plate. The peel force relates to a required force to peel the first adhesive layer off the skin surface. The peeling distance is with respect to one end of the first adhesive layer where the peel force starts to be exercised. The peeling distance relates to the size or length of the first adhesive layer and thereby may relate to a size or length of a portion the first adhesive layer affected by moisture and of a portion of the first adhesive layer not affected by moisture. The peel forces illustrated in FIGS. 18A-18B are representative of adhesive performance of the first adhesive layer of the base plate to the skin surface.

Composition of the first adhesive layer of the base plate as disclosed herein in one or more embodiment is formulated to provide adhesion of the base plate to the skin surface of the user when the base plate is worn and to maintain a dry and healthy skin surface. Avoiding maceration of skin when occluding the skin with an adhesive is done by transporting sweat away from the skin and into the first adhesive layer by means of e.g. hydrocolloid types and adhesive (e.g. hydrocolloid adhesives) forming part of an absorbing element of the first adhesive layer.

For example, when the absorbing element is in contact with moisture, (e.g. water, sweat, urine or faeces), the absorbing element absorb the moisture. This reduces the adhesion of the first adhesive layer to the skin.

For example, the first adhesive layer goes from a dry adhesive state with acceptable adhesive performance (e.g. acceptable adhesion and cohesion) in to a wet adhesive state (e.g. reduced or non-adhesion and low cohesion gel).

Curve 1602 of FIGS. 18A and 18B shows a peel force applied to the first adhesive layer as a function of a peeling distance travelled by a peeling action exercising the peel force on the first adhesive layer in a dry adhesive state, (e.g. not affected by moisture). The peel force is expressed in Newtons while the peeling distance is expressed in mm. The length of the first adhesive layer in dry adhesive state is illustrated by X5, corresponding to length of the first adhesive layer 1608 in dry adhesive state.

Curve 1602 shows that the peel force applied to the first adhesive layer in a dry adhesive state is equal to Y1 when the peeling distance is less than X1. At X1, the peeling force drops as the peeling distance increases towards X5 and the end of the first adhesive layer.

Curve 1604 of FIG. 18A shows a peel force applied to the first adhesive layer as a function of a peeling distance travelled by a peeling action exercising the peel force on the first adhesive layer in a wet adhesive state, (e.g. affected by moisture to the point of reaching a completely wet adhesive state, where the first adhesive layer has become a gel).

Curve 1604 shows that when the peeling distance is less than X2, the peel force applied to the first adhesive layer in a wet adhesive state is equal to Y2 which has much lower value than Y1. This shows that the adhesive performance of the first adhesive layer is reduced when the first adhesive layer is in a wet adhesive state. At X2, the peeling force drops as the peeling distance increases until the end of the first adhesive layer. It is noted that X2 is larger than X1, because the first adhesive layer in a wet adhesive state extends in volume, and thus in length due to the gelling of the components of the first adhesive layer.

The peel experiment illustrated in FIG. 18A shows a loss of adhesive performance when the first adhesive is in a wet adhesive state.

Curve 1606 of FIG. 18B shows a peel force applied to the first adhesive layer as a function of a peeling distance travelled by a peeling action exercising the peel force on the first adhesive layer illustrated 1610 which comprises a first portion 1610A in a dry adhesive state and a second portion 1610B in a wet adhesive state, (e.g. affected by moisture to the point of reaching a completely wet adhesive state, where the first adhesive layer has become a gel).

Curve 1606 shows that when the peeling distance is less than X3, the peel force applied to the first adhesive layer in a wet adhesive state is equal to Y3 which has lower value than Y1. This shows that the adhesive performance of the first adhesive layer is reduced when the first adhesive layer comprises a portion in a wet adhesive state. At X3, the peeling force drops as the peeling distance increases until the end of the first adhesive layer. It is noted that X3 corresponds to the length of the portion 1610A in dry adhesive state.

The peel experiment illustrated in FIG. 18B shows a loss of adhesive performance when the first adhesive is partly in a wet adhesive state.

Accordingly, FIG. 18A-18B demonstrate that the operating state determined based on monitor data is indicative of adhesive performance of the base plate.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly, to be regarded in an illustrative rather than restrictive sense. The claimed invention is intended to cover all alternatives, modifications and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stoma-receiving opening
19 opening center
20 docking station
22 first connector
24 docking station user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
218 masking element
218A distal surface of masking element
218B proximal surface of masking element
220 electrode configuration 222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
300 method for communicating the leakage state of the ostomy appliance
301 obtaining monitor data from the one or more devices
301a obtaining the monitor data indicative of the presence of fluid at the proximal side of a first adhesive layer of the base plate
301b obtaining data representative of detection of fluid on the proximal side in the primary sensing zone and the secondary sensing zone
301c obtaining localized monitor data
302 determining a leakage state of the ostomy appliance based on the monitor data
302a determining a leakage location and/or a leakage time information
302b determining one or more moisture pattern types based on the monitor data
302bb identifying a moisture pattern type based on parameter data
302c deriving the leakage state based on the one or more moisture pattern types
303 communicating the leakage state of the ostomy appliance via the interface
303a displaying, on a visual interface of the accessory device, a user interface comprising a user interface object representative of the leakage state
303b notifying the user via the interface
303c communicating the leakage state of the ostomy appliance to the server device
401 accessory device memory
402 accessory device processor
403 accessory device interface
500 user interface
502 first ring
502a first primary ring part
502b first secondary ring part
502c first tertiary ring part
504 second ring
504a second secondary ring part
504b second secondary ring part
504c second tertiary ring part
506 third ring
506a third primary ring part
506b third secondary ring part
506c third tertiary ring part
508 central circle
510 text prompt
512 first angular delimiter
514 second angular delimiter
516 third angular delimiter
522 first circle
524 second circle
526 third circle
1000 curve representing the upper voltage threshold value
1002 curve representing the medium voltage threshold value
1004 curve representing the lower voltage threshold value
1006 curve representing a gradient limit
1100 curve showing, as a function of time, first parameter data indicative of voltage measured by the first electrode pair of the base plate
1102 curve showing, as a function of time, second parameter data indicative of voltage measured by the second electrode pair of the base plate
1104 curve showing, as a function of time, third parameter data indicative of voltage measured by the third electrode pair of the base plate
1108 curve showing, as a function of time, fourth primary parameter indicative of voltage measured by the fourth electrode pair of the base plate
1110 curve showing, as a function of time, a gradient of fourth primary parameter indicative of voltage gradient
1112 curve showing, as a function of time, a gradient of fourth secondary parameter indicative of voltage gradient measured
1114 curve showing, as a function of time, a gradient of fourth tertiary parameter indicative of voltage gradient measured
1116 curve showing, as a function of time, a fourth secondary parameter indicative of voltage measured 1118 curve showing, as a function of time, a fourth tertiary parameter indicative of voltage measured
1200 curve showing, as a function of time, third parameter data indicative of voltage measured by the third electrode pair of the base plate
1202 curve showing, as a function of time, first parameter data indicative of voltage measured by the first electrode pair of the base plate
1204 curve showing, as a function of time, second parameter data indicative of voltage measured by the second electrode pair of the base plate
1206 curve showing, as a function of time, a fourth primary parameter indicative of voltage measured by the fourth electrode pair of the base plate
1208 curve showing, as a function of time, a fourth secondary parameter indicative of voltage measured
1210 curve showing, as a function of time, a fourth tertiary parameter indicative of voltage measured
1212 curve showing, as a function of time, a gradient of fourth primary parameter indicative of voltage gradient measured by the fourth electrode pair of the base plate
1214 curve showing, as a function of time, a gradient of fourth secondary parameter data indicative of voltage gradient measured
1216 curve showing, as a function of time, a gradient of fourth tertiary parameter indicative of voltage gradient measured
1300 curve showing, as a function of time, first parameter data indicative of voltage measured by the first electrode pair of the base plate
1302 curve showing, as a function of time, second parameter data indicative of voltage measured by the second electrode pair of the base plate
1304 curve showing, as a function of time, third parameter data indicative of voltage measured by the third electrode pair of the base plate
1306 curve showing, as a function of time, a fourth primary parameter indicative of voltage measured by the fourth electrode pair of the base plate
1308 curve showing, as a function of time, a fourth secondary parameter indicative of voltage measured
1310 curve showing, as a function of time, a fourth tertiary parameter indicative of voltage measured
1312 curve showing, as a function of time, a gradient of fourth primary parameter indicative of voltage gradient measured by the fourth electrode pair of the base plate
1314 curve showing, as a function of time, a gradient of fourth secondary parameter indicative of voltage gradient measured
1316 curve showing, as a function of time, a gradient of fourth tertiary parameter indicative of voltage gradient measured
1502 curve showing, as a function of time, first parameter data indicative of voltage measured by the first electrode pair of the base plate
1504 curve showing, as a function of time, second parameter data indicative of voltage measured by the second electrode pair of the base plate
1506 curve showing a diameter of the white ring as a function of time
1602 curve showing peel force applied to the first adhesive layer in a dry adhesive state as a function of peeling distance
1604 a peel force applied to the first adhesive layer as a function of a peeling distance travelled by a peeling action exercising the peel force on the first adhesive layer in a wet adhesive state
1606 a peel force applied to the first adhesive layer as a function of a peeling distance travelled by a peeling action exercising the peel force on the first adhesive layer partially wet
1608 length of the first adhesive layer 1608 in dry adhesive state
1610 the first adhesive layer which comprises a first portion in a dry adhesive state and a second portion in a wet adhesive state
1610A a first portion in a dry adhesive state
1610B a second portion in a wet adhesive state

The invention claimed is:

1. A method, performed in an accessory device, for determining a leakage state of an ostomy appliance comprising a base plate configured to be placed on a skin surface of a user, the base plate comprising a plurality of electrodes, wherein the accessory device comprises a wireless interface configured to communicate with a monitor device of an ostomy system comprising the ostomy appliance, the method comprising:
obtaining monitor data, from the monitor device, that is indicative of presence of fluid at one or more sensing zones of the base plate at a proximal side of a first adhesive layer of the base plate towards the skin surface, the monitor data relating to:
a primary sensing zone of the base plate, comprising at least a first leakage electrode and a second leakage electrode of the plurality of electrodes; and
a secondary sensing zone of the base plate, comprising at least a third leakage electrode and a fourth leakage electrode of the plurality of electrodes;
determining the leakage state of the base plate based on the monitor data for the primary and secondary sensing zones of the base plate; and
displaying a representation of the leakage state of the base plate via a user interface of the accessory device, wherein the representation of the leakage state comprises an indication of the one or more sensing zones that are associated with the presence of fluid.

2. The method according to claim 1, the method comprising:
determining whether the leakage state is indicative of leakage risk; and
displaying the representation of the leakage state when the leakage state fulfils leakage criterion.

3. The method according to claim 1, wherein the ostomy appliance comprises an ostomy pouch and the base plate comprising the first adhesive layer that has the first proximal side, and wherein obtaining monitor data comprises obtaining monitor data from the base plate, the monitor data being indicative of the presence of fluid at the proximal side of the first adhesive layer of the base plate.

4. The method according to claim 1, wherein the monitor data comprises ostomy data and/or parameter data.

5. The method according to claim 4, wherein the ostomy data and/or the parameter data are indicative of resistance between any two of the plurality of electrodes, capacitance and/or inductance between any two of the plurality of electrodes, and/or any change in resistance, capacitance, and/or inductance between any two of the plurality of the plurality of electrodes.

6. The method according to claim 4, wherein obtaining the monitor data comprises obtaining localized monitor data with respect to a location and/or zone at the proximal side of the first adhesive layer of the base plate, and/or time information data and wherein determining the leakage state comprises determining a leakage location and/or a leakage time information.

7. The method according to claim 1, wherein determining the leakage state of the ostomy appliance based on the monitor data comprises determining one or more moisture pattern types based on the monitor data.

8. The method according to claim 7, wherein determining the one or more moisture pattern types based on the monitor data comprises identifying a moisture pattern type based on parameter data.

9. The method according to claim 7, wherein it is determined the leakage state is indicative of leakage risk when a leakage of output is identified at the proximal side based on the one or more moisture pattern types.

10. The method according to claim 7, wherein determining the leakage state of the ostomy appliance based on the monitor data comprises deriving the leakage state based on the one or more moisture pattern types.

11. The method according to claim 1, wherein the accessory device comprises an audio interface and/or a transceiver module.

12. The method according to claim 1, wherein the user interface is displayed on a display of the accessory device and the user interface comprises a user interface object representative of the leakage state.

13. The method according to claim 12, wherein the user interface object representative of the leakage state comprises one or more of a first user interface object, and a second user interface object, wherein the first and/or second user interface objects are indicative of one or more of: a first leakage state and a second leakage state.

14. The method according to claim 1, wherein the ostomy system comprises a server device and communicating the leakage state of the ostomy appliance comprises communicating the leakage state of the ostomy appliance to the server device.

15. The method of claim 1, wherein the first leakage electrode is the third leakage electrode.

16. An accessory device, wherein the accessory device is configured to form part of an ostomy system comprising an ostomy appliance comprising a base plate configured to be placed on a skin surface of a user, the base plate comprising a plurality of electrodes, the accessory device comprising:
a memory;
a processor coupled to the memory; and
a wireless interface, coupled to the processor, configured to communicate with a monitor device of the ostomy system;
wherein the wireless interface is configured to obtain monitor data, from the monitor device, that is indicative of presence of fluid at one or more sensing zones of the base plate at a proximal side of a first adhesive layer of the base plate towards the skin surface, the monitor data relating to:
a primary sensing zone of the base plate, comprising at least a first leakage electrode and a second leakage electrode of the plurality of electrodes; and
a second sensing zone of the base plate, comprising at least a third leakage electrode and a fourth leakage electrode of the plurality of electrodes;
wherein the processor is configured to determine a leakage state of the base plate based on the monitor data for the primary and secondary sensing zones of the base plate;
wherein the memory is configured to store the monitor data and/or the leakage state; and
wherein the accessory device provides, to the user, an indication of the leakage state of the base plate, wherein the indication includes the one or more sensing zones that are associated with the presence of fluid.

17. The accessory device of claim 16, wherein:
the processor is further configured to determine whether the leakage state is indicative of leakage risk; and
the accessory device provides the indication when the leakage state fulfils leakage criterion.

18. An ostomy appliance system comprising:
an ostomy appliance comprising a base plate configured to be placed on a skin surface of a user, the base plate comprising a plurality of electrodes; and
a monitor device comprising a wireless interface configured to communicate with an accessory device, wherein the monitor device is configured to:
obtain ostomy data from the plurality of electrodes of the base plate, wherein the ostomy data is indicative of a resistance between any two of the plurality of electrodes;
process the ostomy data to generate monitor data indicative of a presence of liquid at one or more sensing zones of a proximal side of a first adhesive layer of the base plate, wherein the proximal side of the first adhesive layer is towards the skin surface and the monitor data relates to:
a primary sensing zone comprising at least a first electrode and a second electrode of the plurality of electrodes; and
a secondary sensing zone comprising at least a third electrode and a fourth electrode of the plurality of electrodes; and
provide, via the wireless interface, the monitor data for the primary and secondary sensing zones of the base plate to the accessory device, thereby causing the accessory device to display a representation of a leakage state associated with the base plate, wherein the representation of the leakage state comprises an indication of the one or more sensing zones that are associated with the presence of liquid.

19. A computer readable storage device storing a set of instructions that, when executed by an accessory device with a communication interface, a memory, and a processor, cause the accessory device to perform a set of operations, comprising:
obtaining monitor data from a monitor device of an ostomy system, the monitor data comprising ostomy data obtained, by the monitor device, from a plurality of electrodes of a base plate of the ostomy system, the monitor data being indicative of presence of fluid at one or more sensing zones of a side of a first adhesive layer of the base plate that is placed towards a skin surface of a user, wherein the monitor data relates to:
a primary sensing zone of the base plate, comprising at least a first leakage electrode and a second leakage electrode of the plurality of electrodes; and
a secondary sensing zone of the base plate, comprising at least a third leakage electrode and a fourth leakage electrode of the plurality of electrodes;
determining a leakage state of the base plate based on the monitor data for the primary and secondary sensing zones of the base plate; and
displaying a representation of the leakage state of the base plate via a user interface of the accessory device, wherein the representation of the leakage state comprises an indication of the one or more sensing zones that are associated with the presence of fluid.

20. The computer readable storage device of claim 19, wherein the set of operations further comprises:
- determining whether the leakage state is indicative of leakage risk; and
- displaying the representation of the leakage state when the leakage state fulfils leakage criterion.

* * * * *